United States Patent
Voss et al.

(10) Patent No.: US 9,624,253 B2
(45) Date of Patent: Apr. 18, 2017

(54) METHOD FOR PURIFYING A TARGET NUCLEIC ACID

(75) Inventors: Thorsten Voss, Hilden (DE); Ralf Wyrich, Hilden (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 13/810,406

(22) PCT Filed: Jul. 15, 2011

(86) PCT No.: PCT/EP2011/062124
§ 371 (c)(1),
(2), (4) Date: Jan. 15, 2013

(87) PCT Pub. No.: WO2012/007569
PCT Pub. Date: Jan. 19, 2012

(65) Prior Publication Data
US 2013/0122574 A1    May 16, 2013

(30) Foreign Application Priority Data

Jul. 15, 2010 (EP) .................................... 10007346

(51) Int. Cl.
C07H 1/08 (2006.01)
C12N 15/10 (2006.01)

(52) U.S. Cl.
CPC ........... *C07H 1/08* (2013.01); *C12N 15/1006* (2013.01)

(58) Field of Classification Search
None
See application file for complete search history.

(56) References Cited

U.S. PATENT DOCUMENTS

| | | | |
|---|---|---|---|
| 6,861,213 B2* | 3/2005 | Oelmuller et al. | 435/5 |
| 7,683,035 B1* | 3/2010 | Erbacher et al. | 514/44 R |
| 7,824,855 B2* | 11/2010 | Inomata et al. | 435/6.1 |
| 7,884,201 B2* | 2/2011 | Inomata et al. | 536/25.4 |
| 8,624,020 B2* | 1/2014 | Himmelreich et al. | 536/25.4 |
| 2005/0112656 A1* | 5/2005 | Iwaki | 435/6 |
| 2008/0113356 A1* | 5/2008 | Sasaki et al. | 435/6 |
| 2008/0207889 A1* | 8/2008 | Sprenger-Haussels et al. | 536/25.4 |

FOREIGN PATENT DOCUMENTS

| | | |
|---|---|---|
| EP | 1690938 A1 | 8/2006 |
| EP | 2128169 A1 | 12/2009 |
| WO | 02/00600 A1 | 1/2002 |

OTHER PUBLICATIONS

Wolfe, Kelley A; et al; "Toward a microchip-based solid-phase extraction method for isolation of nucleic acids" Electrophoresis, 23, 727-733, 2002.*
RNeasy Mini Handbook, Qiagen, May 1999.*
QIAsymphony PAXgene®—Blood RNA Kit Handbook, PreAnalytiX (32 pages) (Sep. 2008).

* cited by examiner

Primary Examiner — Renee Claytor
Assistant Examiner — David Berke-Schlessel
(74) Attorney, Agent, or Firm — Seed IP Law Group LLP

(57) ABSTRACT

The present invention pertains to method for purifying at least a target nucleic acid from a sample, said method comprising at least the following steps: a) incubating the sample with at least one protein-degrading compound; b) binding the target nucleic acid to a solid phase; c) eluting the target nucleic acid from the solid phase; d) incubating the eluted target nucleic acid with at least one protein-degrading compound; e) binding the target nucleic acid again to a solid phase; f) optionally eluting the bound target nucleic acid from the solid phase. It was surprisingly found that performing a second protein digestion step after the target nucleic acid was bound and eluted from a solid phase before the nucleic acids are rebound to a solid phase is very efficient in reducing remaining protein contaminations in the isolated nucleic acid.

23 Claims, 14 Drawing Sheets

Figure 3:
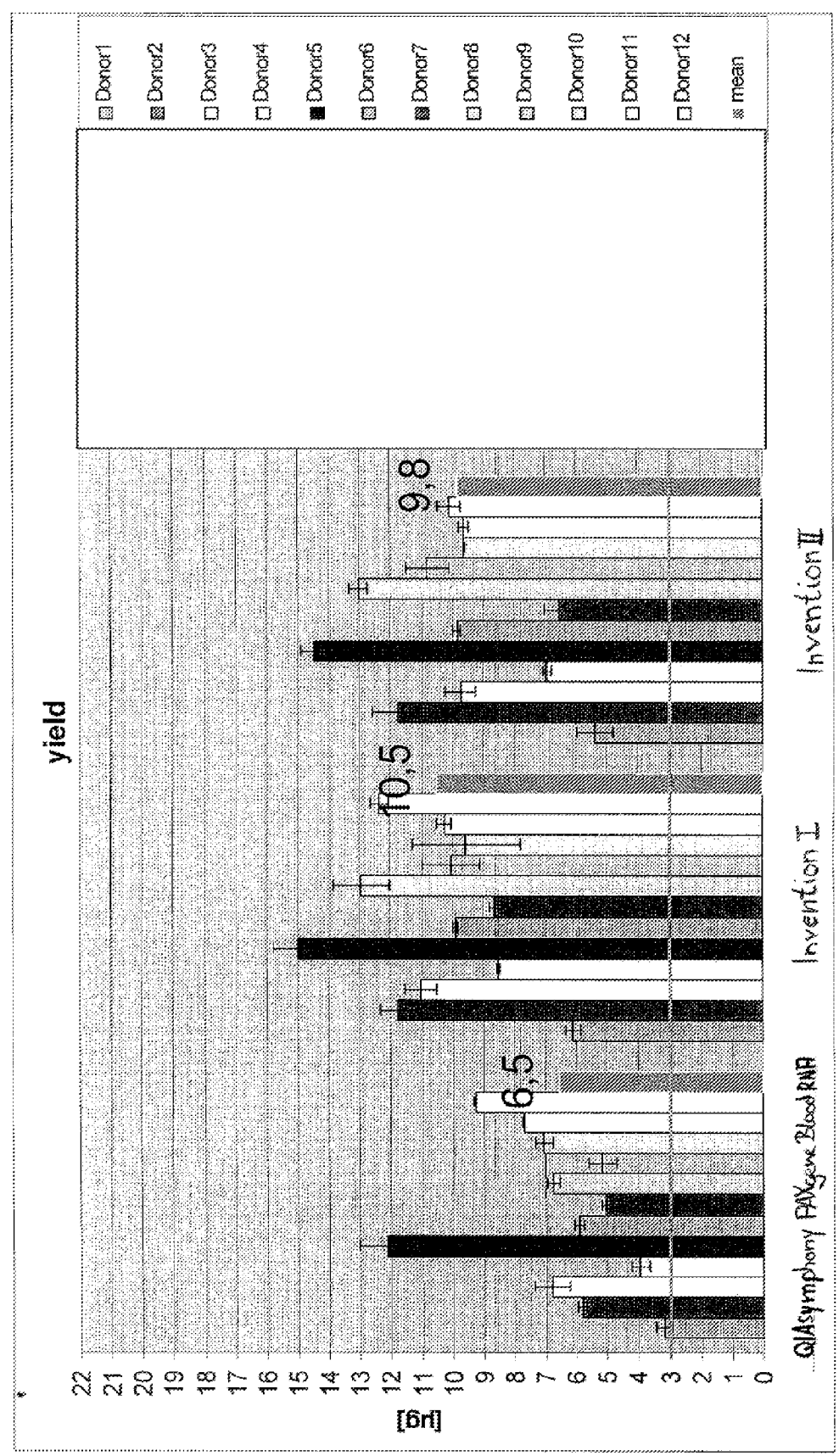

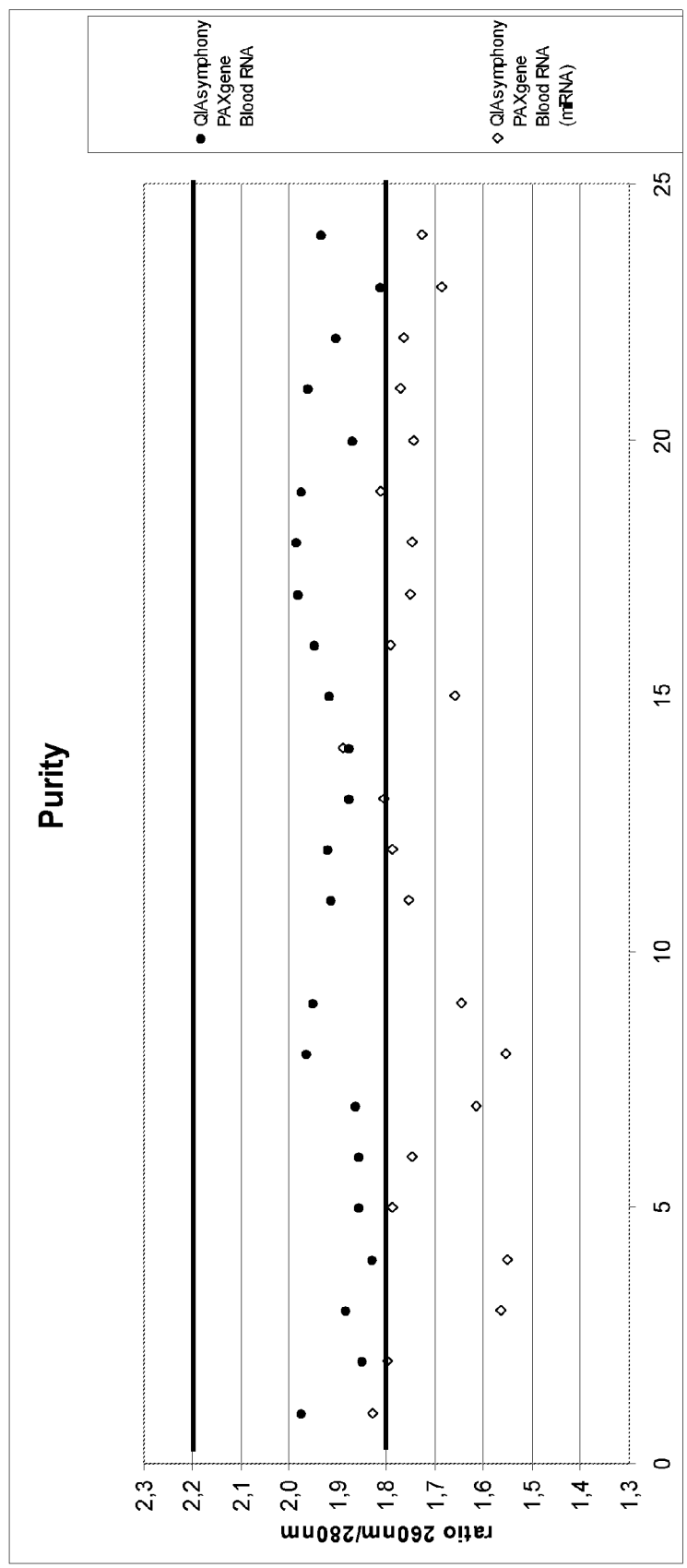
Fig. 1.1

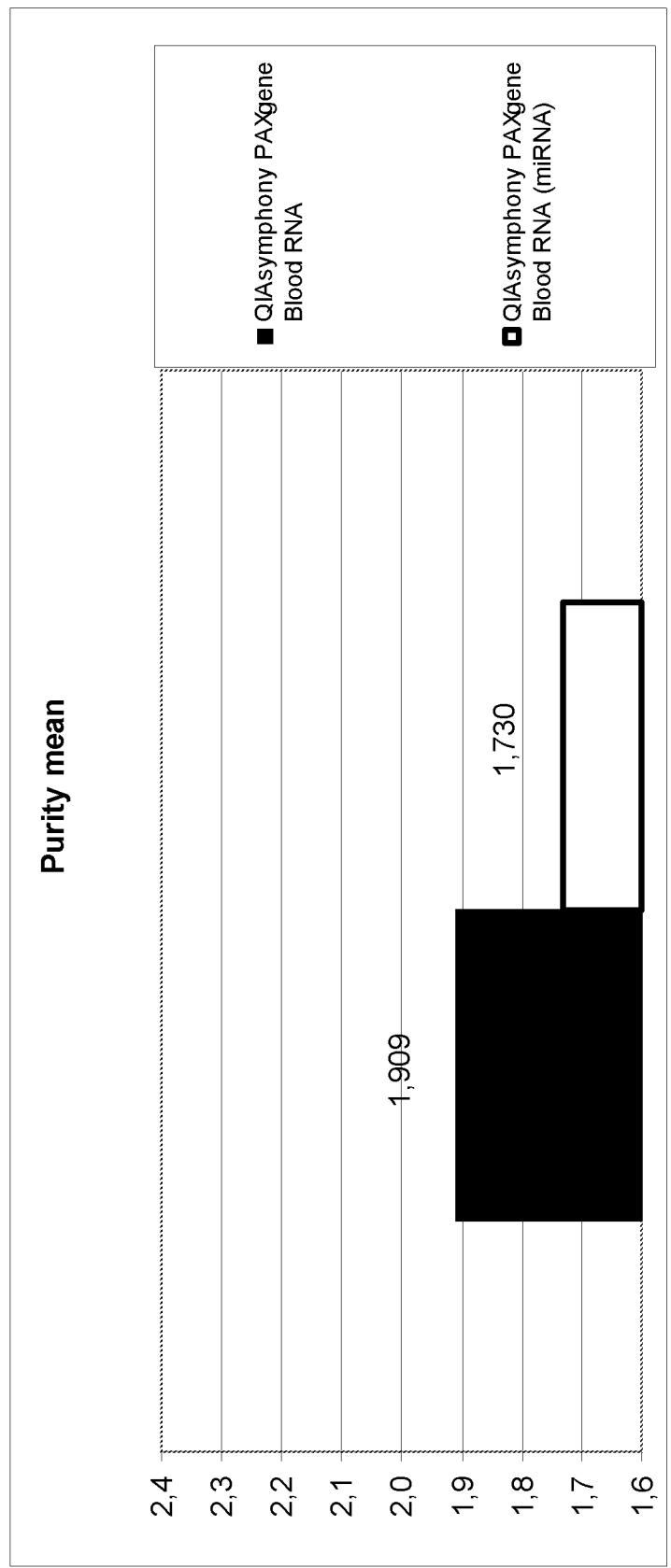
Fig. 1.2

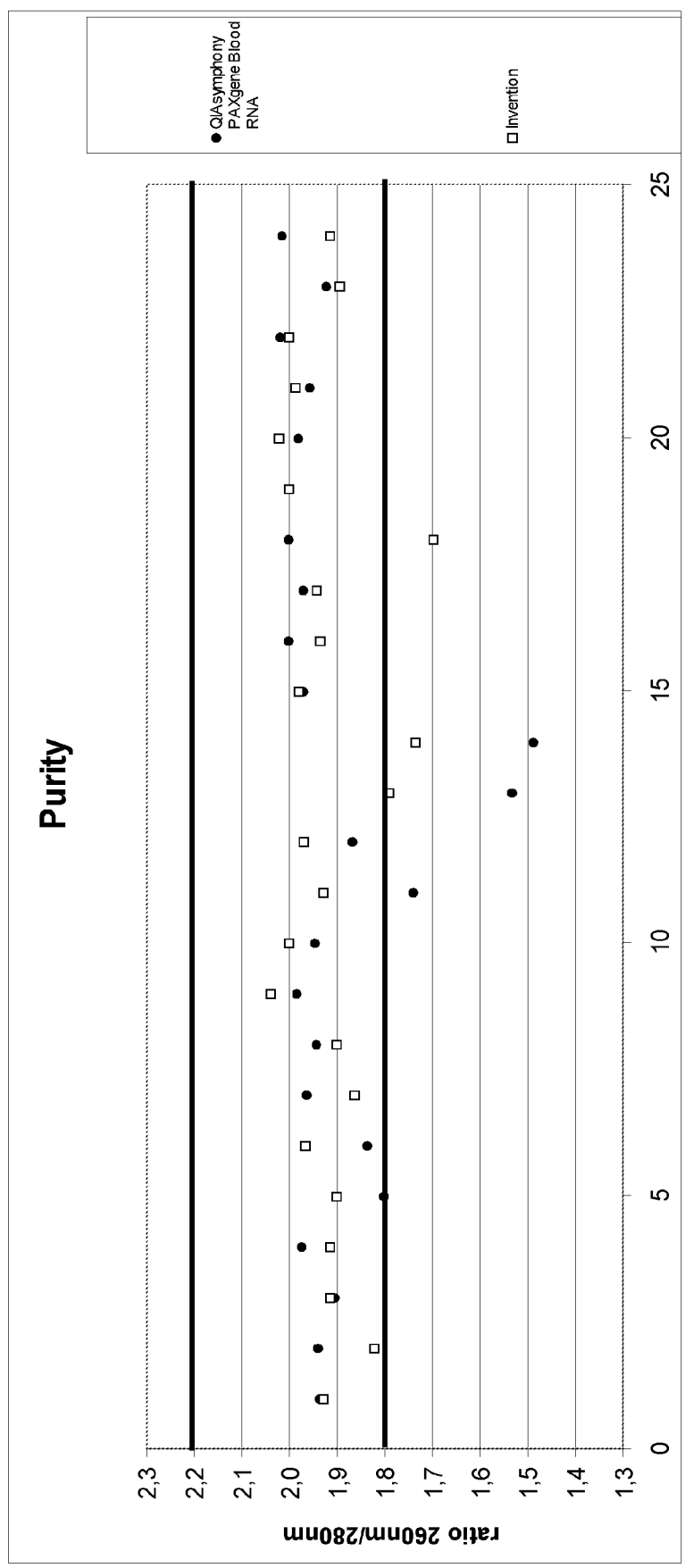
Fig. 2.1

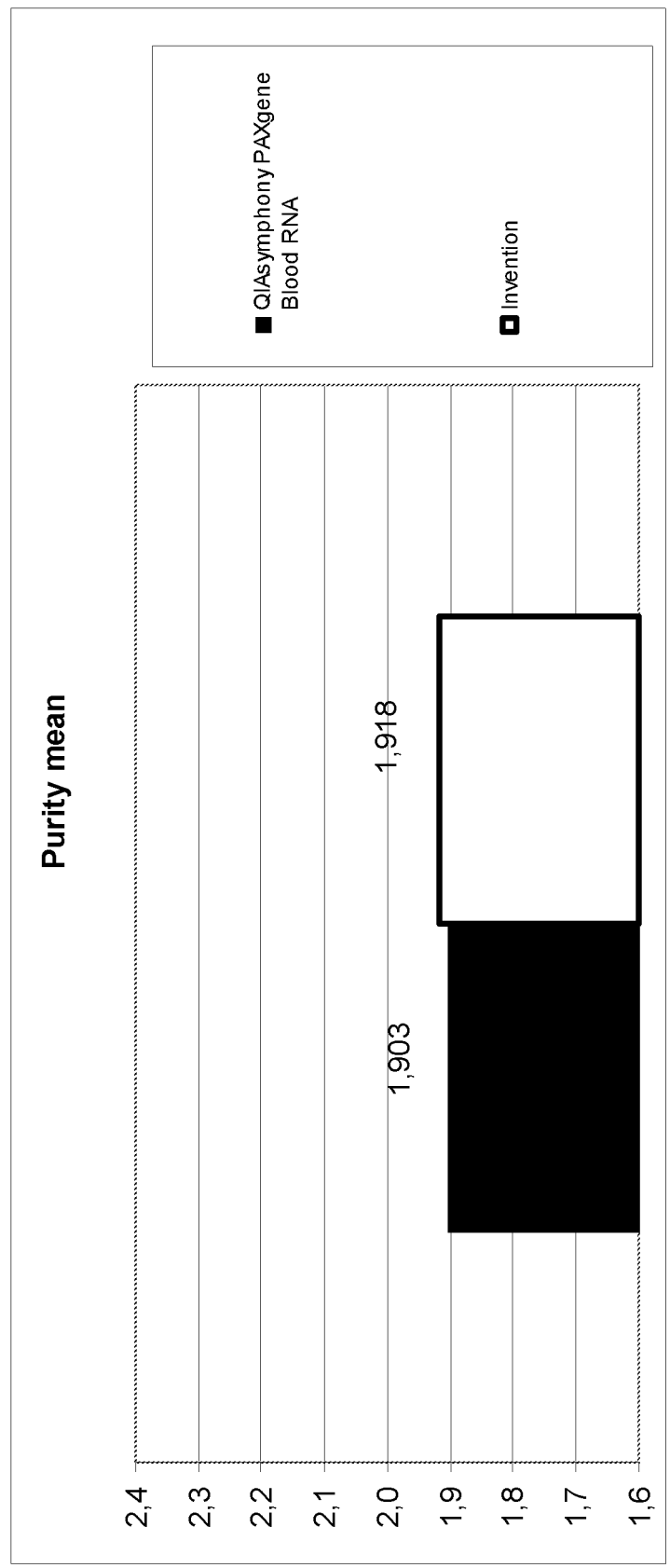
Fig. 2.2

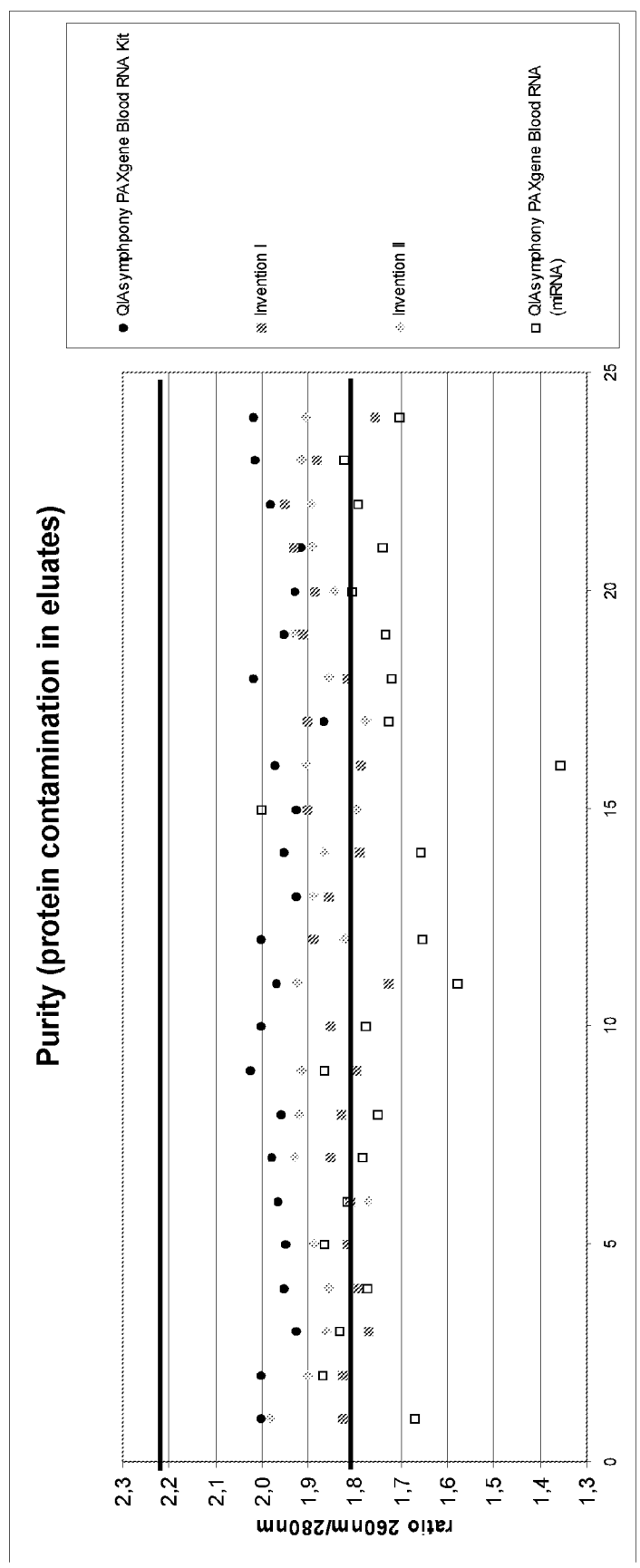
Fig. 5.1.1

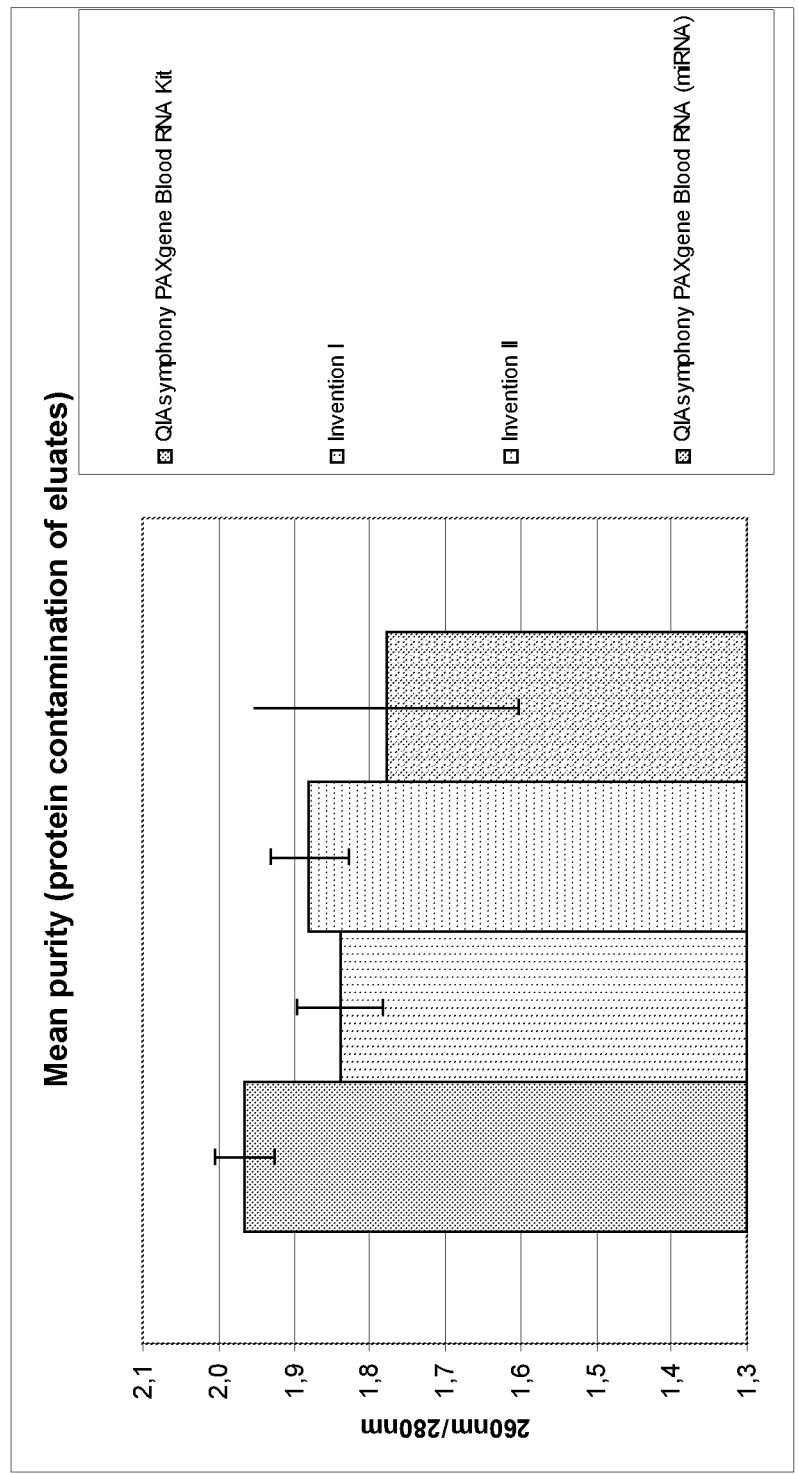
Fig. 5.1.2

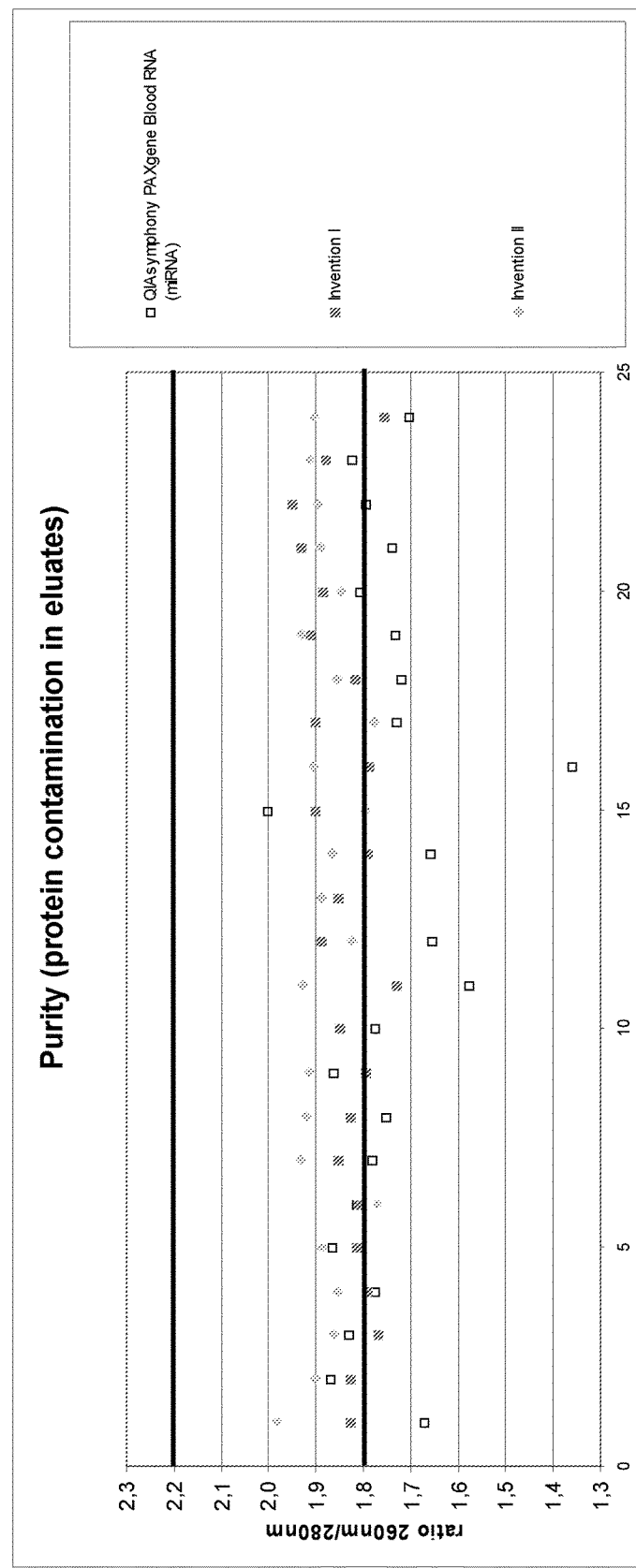
Fig. 5.2.1

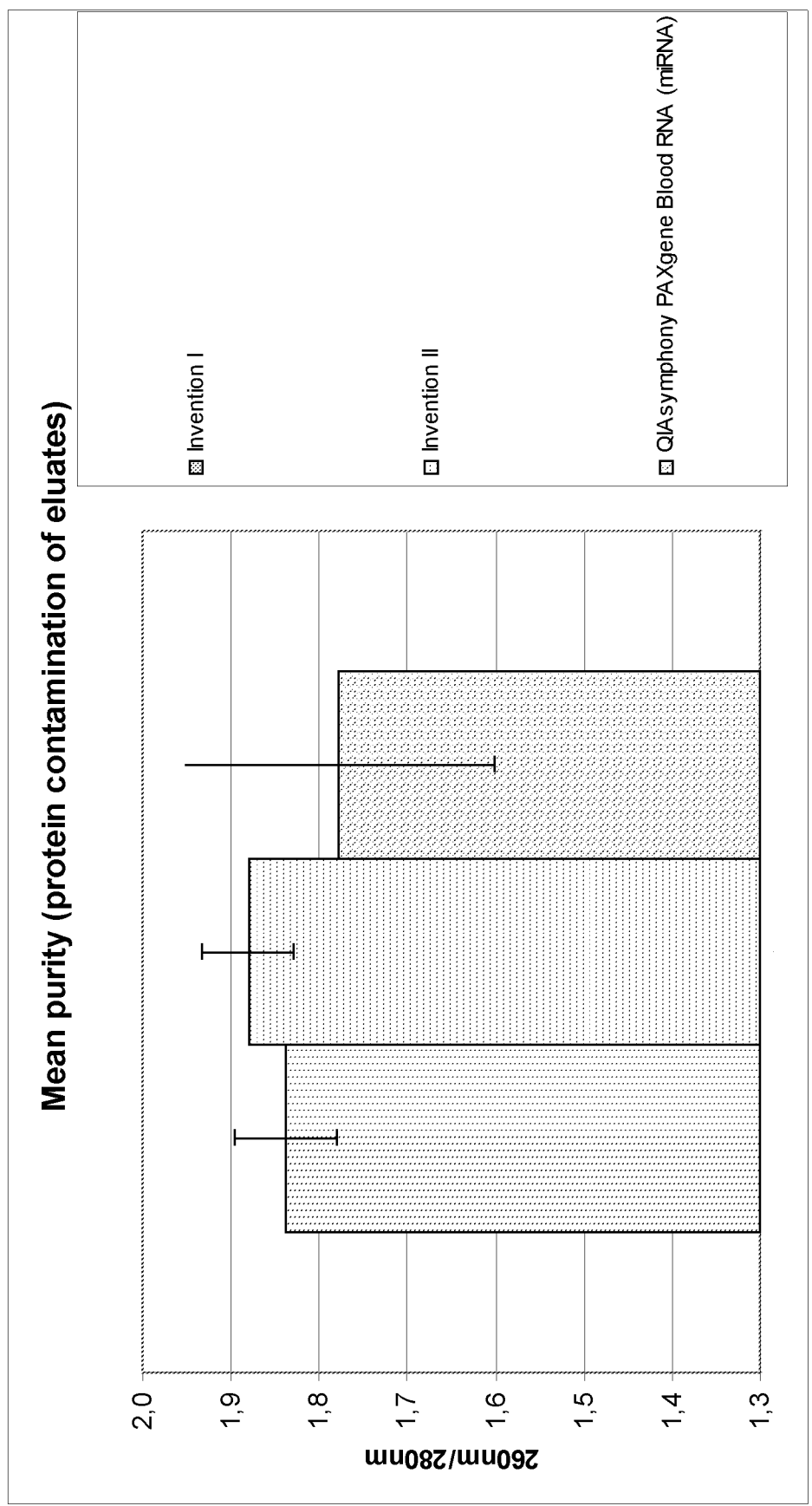
Fig. 5.2.2

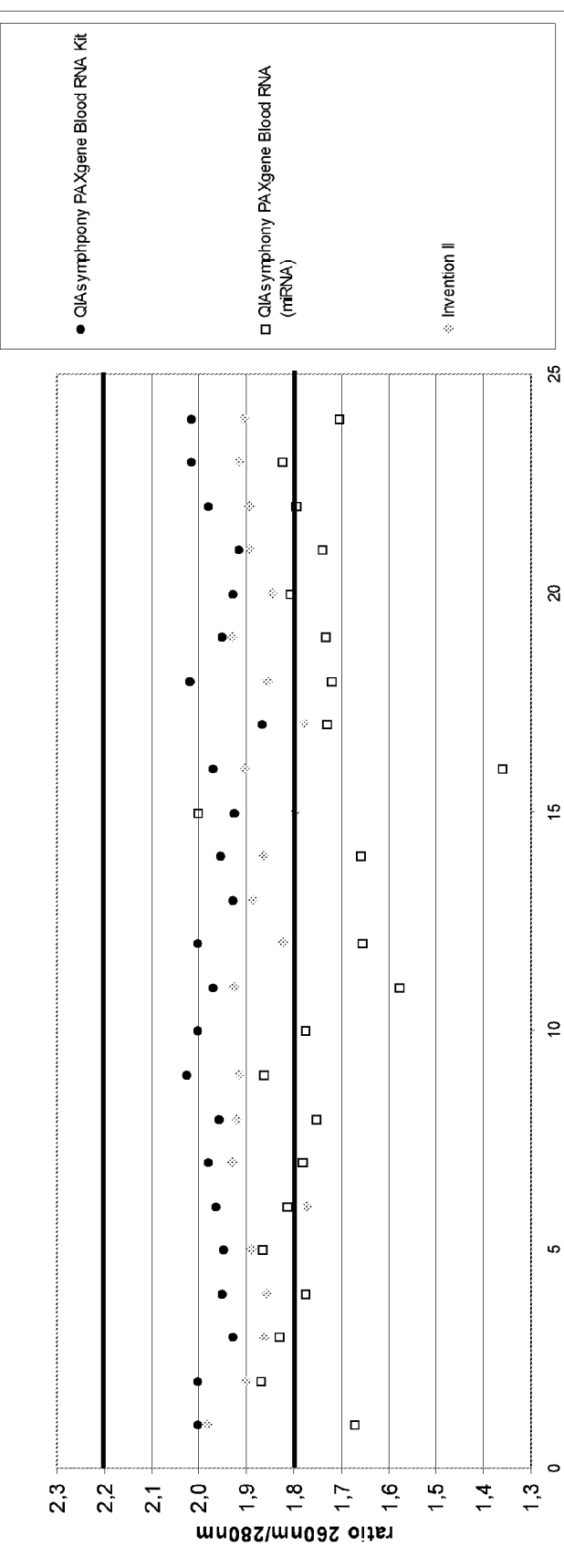
Fig. 5.3.1

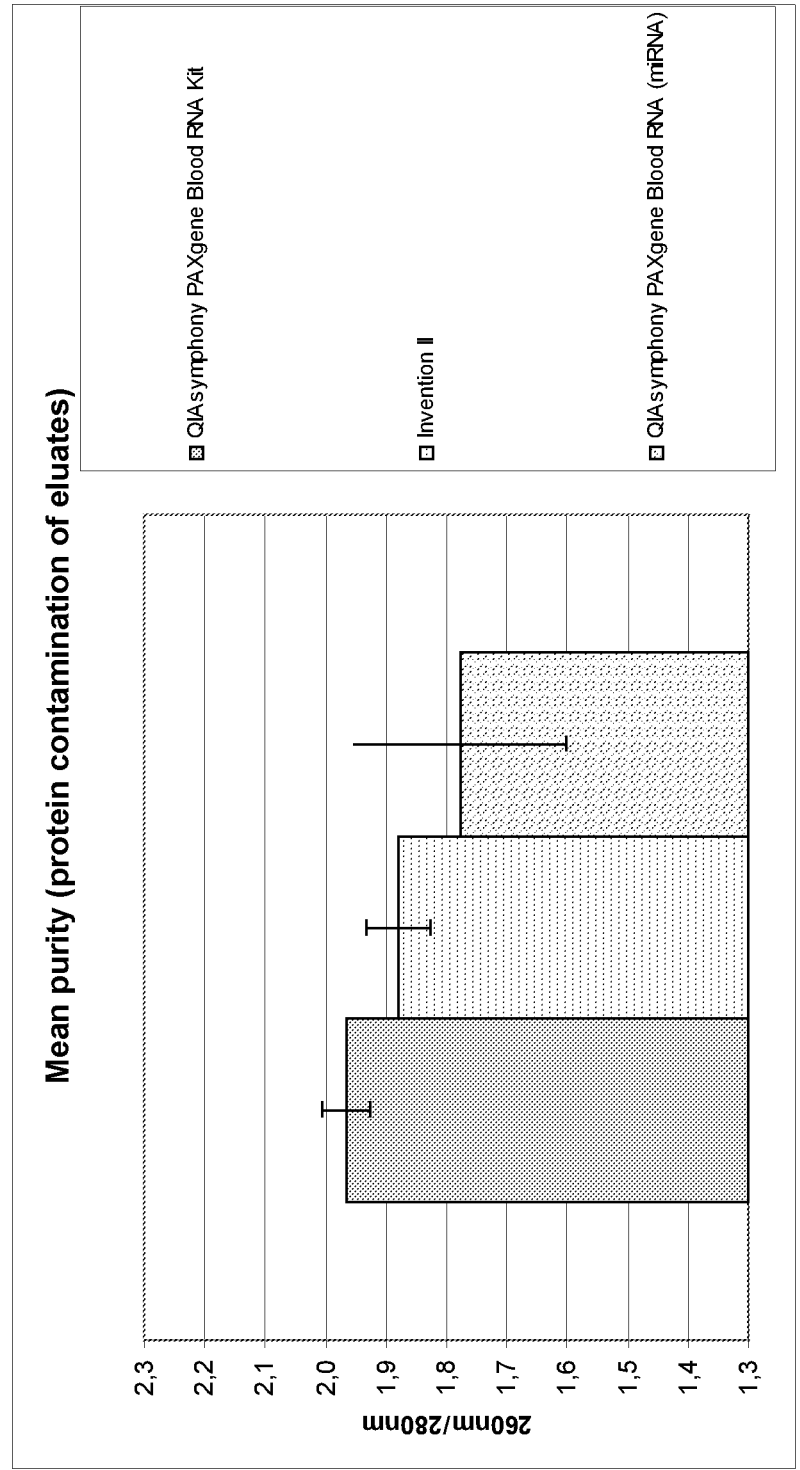

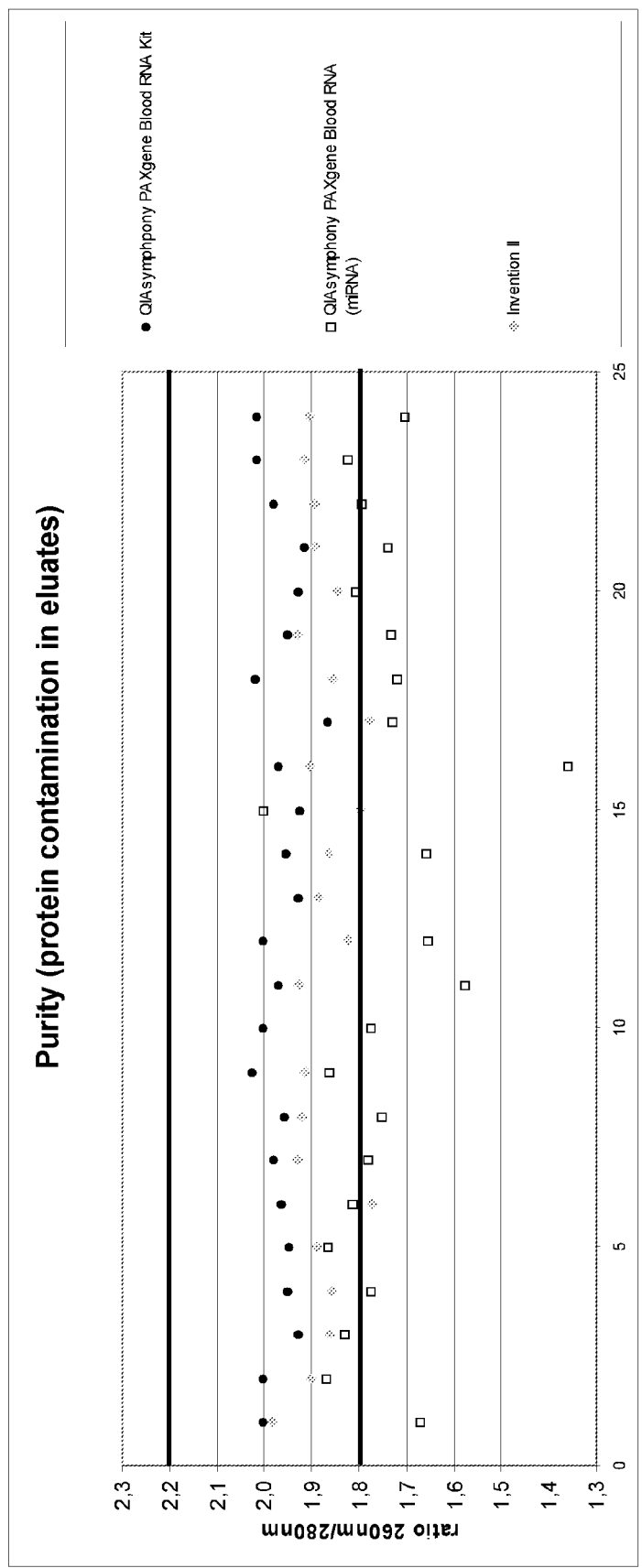
Fig. 5.4.1

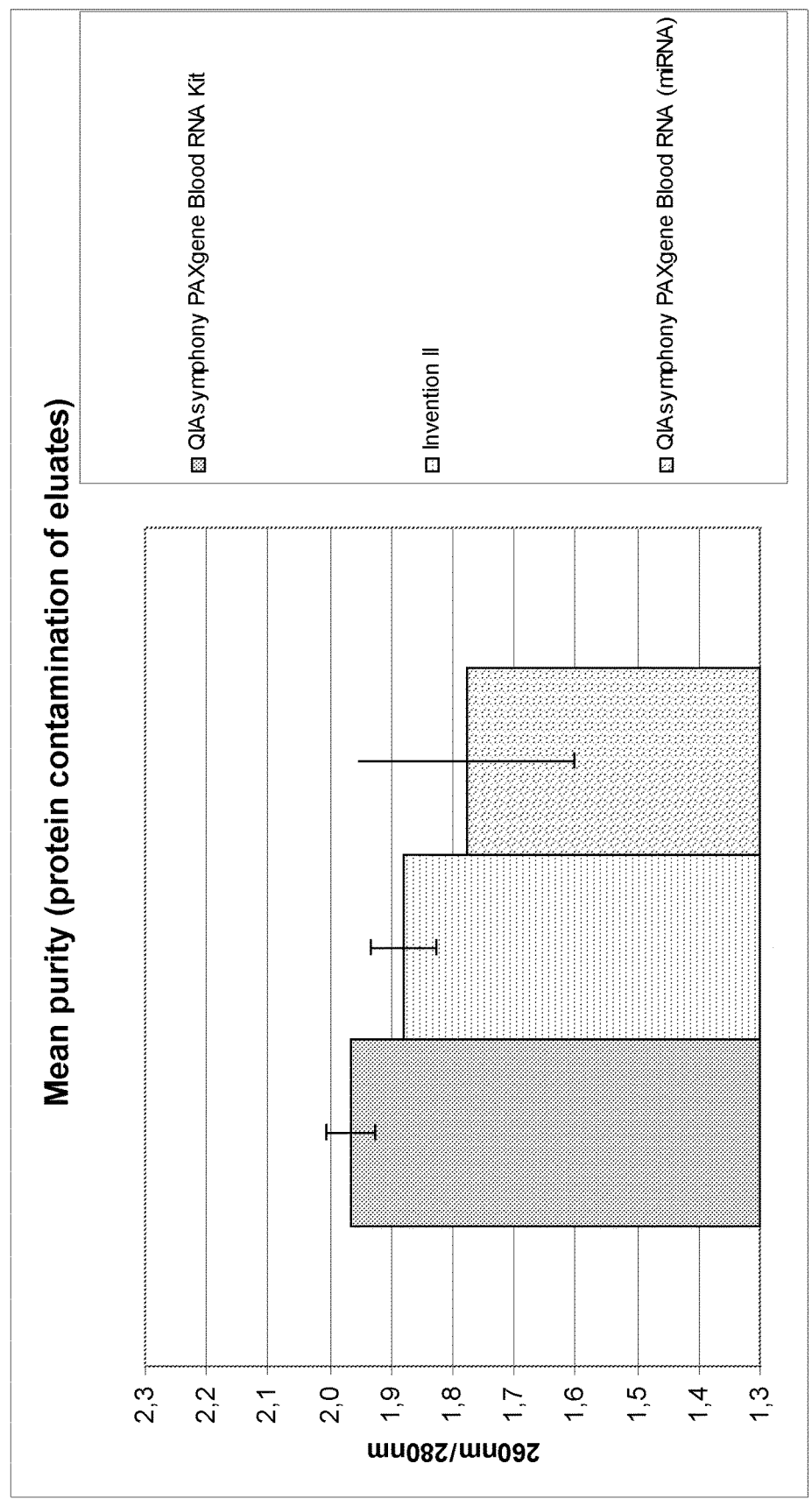
Fig. 5.4.2

METHOD FOR PURIFYING A TARGET NUCLEIC ACID

The work leading to this invention has received funding from the European Community's Seventh Framework Programme (FP7/2007-2013) under grant agreement n° 222916.

The present invention pertains to methods for isolating at least a target nucleic acid, preferably RNA, from a sample with high purity.

When isolating a target nucleic acid from a sample it is desirous to obtain the target nucleic acid with high purity. Therefore, contaminants such as in particular proteins and other compounds that potentially interfere with the subsequent use of the target nucleic acid are supposed to be removed during the purification process. Furthermore, the purification methods shall ensure that the target nucleic acid to be isolated is not degraded during the purification process.

Several methods for isolating nucleic acids are known in the prior art. To remove proteins comprised in the samples it is common to degrade the proteins during lysis of the sample using proteolytic enzymes. When purifying DNA, the DNA is protected during lysis from degradation by DNases usually by inactivating the co-factors necessary for the activity of the DNase using suitable chelators in the lysis buffers. The isolation of RNA is particularly challenging, because RNAses are omnipresent in rather high amounts and are active over a broad temperature range and usually do not need co-factors for their activity. Thus, a specific inactivation of the RNAses during lysis is not possible. In order to inactivate and degrade RNAses it is therefore common to perform the lysis by using strong denaturing lysis reagents such as for example phenol and/or chaotropic agents.

After lysis of the sample and degradation of the proteins, the nucleic acids are purified. For isolating the target nucleic acid with high purity the nucleic acids are usually bound to a solid phase, washed several times in order to remove protein and other impurities and the nucleic acids are then eluted.

However, the presently available methods for isolating nucleic acids are often not optimal with respect to the achieved purity grade because the isolated nucleic acids often comprise in particular protein contaminations. Protein contaminations in the isolated nucleic acid may cause problems in the intended downstream applications of the isolated nucleic acid. E.g. amplification reactions, cDNA synthesis, in vitro transcription reactions, and labelling reactions may be substantially disturbed by protein contaminations. Therefore, protein contaminations are to be avoided.

However, it is very common for nucleic acid preparations that proteins are co-purified. This is particularly the case when isolating nucleic acids from samples which comprise rather large amounts of protein (such as for example blood, plasma, sputum, saliva or stool) and wherein the protein content varies from sample to sample. E.g. when processing blood or blood products, the protein content in the sample may vary from donor to donor and may also vary within samples taken from the same donor at different points in time. A further important example of a nucleic acid isolation procedure where protein contaminants in the isolated target nucleic acid cause problems, are nucleic acid isolation procedures wherein strong binding conditions are used e.g. in order to ensure optimal binding of the target nucleic acid to the solid phase to isolate the nucleic acids with high yield or wherein e.g. specific nucleic acids are supposed to be (co-)purified which only bind to the solid phase under harsh and thus strong binding conditions. An example for a respective purification method is the isolation of total RNA which includes small RNAs such as micro RNAs. For these purposes, strong binding conditions are necessary to efficiently bind the target nucleic acids to the solid phase such as e.g. high concentrations of alcohol and salts for binding RNA including small RNAs. Under such strong binding conditions, also proteins bind efficiently to the solid phase and protein contaminations are accordingly regularly present in the isolated RNA even if a protein degradation step is performed during lysis and even if several washing steps are performed after the RNA was bound to the solid phase. Due to the strong binding conditions used, protein contaminations are regularly found in the isolated target nucleic acids. The above described problems are further exacerbated in case large sample volumina (e.g. 2.5 ml whole blood) are processed.

In order to reduce protein contaminations in the isolated nucleic acids, methods were thus developed in the prior art, wherein the washing conditions were optimised or wherein a proteolytic enzyme such as proteinase K is added to the washing buffer or wherein remaining protein contaminations are digested while being bound to the solid phase by using a proteolytic enzyme. However, even though these methods provide an improvement to existing protocols, there is still a need for improvement and for obtaining the target nucleic acids with a higher purity.

Furthermore, in order to allow the use of the purified nucleic acids in automated processes (wherein e.g. many samples are processed at the same time) it is desirable to provide a nucleic acid isolation procedure that provides nucleic acids with an acceptable purity grade that lies within a given range of acceptable purity even if using strong binding conditions that promote binding of protein contaminations and even if processing sample types wherein the protein content may vary from sample to sample as it is the case e.g. with blood or blood products.

Thus, it is an object of the present invention to provide a reliable method for purifying at least one target nucleic acid from a sample which renders the isolated target nucleic acid with high purity and in particular, with lower protein contaminations.

Furthermore, it is an object of the present invention to provide a reliable method for purifying at least one target nucleic acid from a sample which renders the isolated target nucleic acid with high purity and in particular, with lower protein contaminations when using nucleic acid binding conditions that also promote binding of proteins to the solid phase and/or when isolating the target nucleic acid from samples which comprise high and also varying amounts of proteins such as e.g. blood or blood products.

SUMMARY OF THE INVENTION

The present invention provides a method for purifying at least one target nucleic acid from a sample which provides the isolated target nucleic acid with high purity because protein contaminations are considerably reduced in the isolated nucleic acid.

According to one aspect of the present invention a method for purifying at least one target nucleic acid from a sample is provided, said method comprising at least the following steps
 a) incubating the sample with at least one protein-degrading compound,
 b) binding the target nucleic acid to a solid phase,
 c) eluting the target nucleic acid from the solid phase, d) incubating the eluted target nucleic acid with at least one protein-degrading compound,
e) binding the target nucleic acid again to a solid phase,
f) optionally eluting the bound target nucleic acid from the solid phase.

It was found by the inventors that a method wherein a second protein degrading step is performed after elution of the target nucleic acid provides the target nucleic acid with higher purity because protein contaminations are considerably reduced in the isolated target nucleic acids. After performing said second protein degrading step the target nucleic acid is again bound to a solid phase and is thereby isolated with high purity.

It was found that performing such second protein degradation step after elution of the nucleic acids improves the reduction of protein contaminations compared to methods wherein a second protein digestion step is performed at a different stage of the nucleic acid isolation procedure or compared to methods that try to reduce protein contaminations by changing the washing conditions. Advantageously, the method according to the present invention allows the isolation of the target nucleic acid with high purity within a given purity range even if strong binding conditions are used for binding the target nucleic acid to the solid phase that also promote binding of protein contaminations to the solid phase and/or if processing samples comprising a high and/or a varying amount of protein. Therefore, the method according to the present invention allows the user to use optimal (e.g. strong) binding conditions for binding the target nucleic acids to the solid phase, thereby increasing the yield of target nucleic acids. Furthermore, the method according to the present invention allows the purification of target nucleic acids that only bind efficiently to a solid phase when using strong binding conditions (such as e.g. small RNA species). The protein contaminations that are inevitably co-purified along with the target nucleic acid when using such strong binding conditions are efficiently removed by the second protein degradation step d) of the method of the present invention, thereby providing the target nucleic acid with high purity.

According to a preferred aspect of the present invention, a method for purifying RNA from a sample which comprises at least RNA and DNA is provided, said method comprising at least the following steps
 a) incubating the sample with at least one proteolytic enzyme in the presence of a chaotropic agent and by heating the sample to at least 40° C.,
   removing at least a portion of the DNA by binding DNA to a first solid phase and separating the DNA bound to said first solid phase from the remaining sample comprising the RNA,
 b) binding the RNA to a second solid phase, wherein at least one chaotropic agent and alcohol in a concentration ≥30% v/v is used during this binding step b),
   performing at least one washing step for washing the RNA bound to said second solid phase,
 c) eluting the RNA from said second solid phase,
 d) incubating the eluted RNA with at least one proteolytic enzyme in the presence of a chaotropic agent and by heating the sample to at least 40° C.,
 e) binding the RNA again to a solid phase wherein at least one chaotropic agent and alcohol in a concentration 30% v/v is used during this binding step e),
   performing at least one washing step for washing the RNA bound to the solid phase,
 f) optionally eluting the bound target nucleic acid from the solid phase.

The method according to the present invention, wherein a second protein degradation step is performed after the target nucleic acid was already once bound and eluted from the solid phase before rebinding the target nucleic acid to the solid phase, is in particular useful for isolating RNA from a sample and in particular for isolating RNA which comprises small RNAs such as miRNAs. For binding the RNA to the solid phase, alcohol and chaotropic agents are used. As is outlined in the above introduction, the use of higher concentrations of alcohol and chaotropic agents during binding has the effect that proteins and protein degradation products remaining in the lysed sample after the first protein degradation step are also bound to the solid phase and are therefore co-purified along with the RNA. The method according to the present invention allows reducing considerably these remaining protein contaminations in the isolated RNA. This even if purifying the RNA from difficult samples such as blood or blood products, using strong binding conditions. Therefore, the method according to the present invention provides important advantages over the prior art.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

It was surprisingly found that performing a second protein degradation step after the target nucleic acid was bound and eluted from a solid phase before the nucleic acids are rebound to a solid phase is very efficient in reducing protein contaminations in the isolated nucleic acid.

Therefore, according to first aspect of the present invention, a method for purifying at least one target nucleic acid from a sample is provided, said method comprising at least the following steps
 a) incubating the sample with at least one protein-degrading compound,
 b) binding the target nucleic acid to a solid phase,
 c) eluting the target nucleic acid from the solid phase,
 d) incubating the eluted target nucleic acid with at least one protein-degrading compound,
 e) binding the target nucleic acid again to a solid phase,
 f) optionally eluting the bound target nucleic acid from the solid phase.

The individual steps of the method according to the present invention will be explained in detail below.

In step a), the sample comprising the target nucleic acid is incubated with at least one protein-degrading compound. Thereby, proteins comprised in the sample are degraded. Usually, step a) will be performed during lysis of the sample or after the initial lysis of the sample was performed in case a sample is processed that needs lysis.

In step b), the target nucleic acid is bound to a solid phase. Suitable solid phases and conditions for binding the target nucleic acid thereto are known in the prior art and are also described in further detail below. Preferably, binding conditions are used that allow strong binding of the target nucleic acids to the solid phase in order to purify the target nucleic acid with high yield. As discussed above, when using such strong binding conditions usually also proteins bind to the solid phase in disturbing amounts. The target nucleic acid is usually separated from the remaining sample, respectively the lysate, while being bound to the solid phase. This can be achieved by any means known in the prior art such as e.g. removing the remaining sample by aspiration, centrifugation or by removing the solid phase with the bound target nucleic acids from the remaining sample.

In step c), the target nucleic acid is eluted from the solid phase and thereby is obtained in an eluate. As discussed above, protein contaminations are usually also bound to the solid phase in step b), in particular if strong binding conditions are used and are thereby also eluted in step c).

Step d) defines the essential step of the method of the present invention. According to step d), the eluted target nucleic acid is again incubated with at least one protein degrading compound. Thereby, remaining protein contaminations that were co-purified and eluted together with the target nucleic acid are efficiently degraded and thereby inactivated.

According to step e) of the method of the present invention, the target nucleic acid is then bound again to a solid phase. The target nucleic acid is usually separated in step e) from the remaining sample while being bound to the solid phase. Again, this can be achieved by any means known in the prior art such as e.g. removing the remaining sample by aspiration, centrifugation or by removing the solid phase with the bound target nucleic acids from the remaining sample. The solid phase used in step e) can be identical to or may be the same type of solid phase that was used in step b) but it is also within the scope of the present invention to use a different solid phase. For the ease of handling in particular in automated methods, it is preferred that the solid phase used in step e) is identical to the one that was used in step b). In this case, the solid phase that was used in step b) remains present during step c) and d). The target nucleic acid is then again bound to said solid phase in step e). Suitable binding conditions for binding the target nucleic acid again to the solid phase are known in the prior art and are also described in detail below. This re-binding of the target nucleic acid to the solid phase in step e) ensures that the target nucleic acid is obtained with high yield and furthermore, has the effect that the isolated target nucleic acid comprises considerably less protein contaminations because the protein contaminations that were degraded in step d) can no longer efficiently bind to the solid phase in binding step e). Thereby, the amount of protein contaminations is reduced. Thus, the method according to the present invention allows the purification of at least a target nucleic acid with high yield and high purity.

In optional step f), the target nucleic acid is eluted from the solid phase if desired. Alternatively, the at least one target nucleic acid may also be processed while being bound to the solid phase, depending on the intended downstream application respectively use of the target nucleic acid. In case it is desired to perform an elution step, elution can be performed for example with classical elution solutions such as water, elution buffers, in particular biological buffers such as Tris and preferably elution solutions are used that do not interfere with the intended downstream application. However, it is also within the scope of the present invention to release and thus elute the nucleic acids from the solid phase in step c) and/or e) by other elution means such as e.g. heating.

The method according to the present invention has several advantages. As explained above, there is a strong correlation between the used binding conditions, the target nucleic acid yield that is obtained by a nucleic acid isolation procedure and the amount of protein contaminations in the isolated target nucleic acids. If non-optimal binding conditions are used for binding the target nucleic acid to the solid phase, protein contaminations cause much less problems because under such non-optimal binding conditions the proteins can not bind efficiently to the solid phase and the nucleic acids that are isolated are obtained with a higher purity. However, using such non-optimal binding conditions which provide the target nucleic acids with an acceptable purity have the disadvantage that the yield of target nucleic acid is decreased and furthermore, target nucleic acids that only bind under strong binding conditions (such as e.g. small RNA species) are not at all or not isolated with an acceptable yield. However, when using stronger binding conditions in order to more efficiently bind the target nucleic acids, thereby increasing the yield of isolated target nucleic acid and/or additionally isolating small nucleic acids, this also increases the amount of protein contaminations in the isolated target nucleic acid because proteins bind strongly to the solid phase when using stronger binding conditions. Therefore, when using the methods known in the prior art the skilled person had to make a choice between yield and purity, in particular when processing difficult samples that comprise high and/or varying amounts of proteins. The method according to the present invention solves this dilemma because said method in particular allows the isolation of a target nucleic acid with high yield and high purity also from difficult samples which comprise high and also varying amounts of protein, such as blood, blood products, serum and/or plasma, even if binding conditions are used for binding the target nucleic acid to the solid phase that also promote binding of undesired protein contaminations (in particular if high concentrations of alcohol and chaotropic agents are used for binding the target nucleic acid e.g. in order to bind and isolate RNA including small RNA).

Therefore, the method according to the present invention provides a considerable improvement over the prior art because it allows to isolate the target nucleic acids with high yield and high purity even from difficult samples. As is demonstrated in the examples, the degree of purity of the isolated target nucleic acid is improved by the method of the present invention.

According to one embodiment, the efficient degradation of proteins is promoted during the incubation with the at least one protein-degrading compound in step a) and/or step d). Preferably, the incubation in step a) and/or step d) is performed under heating. Preferably, the sample of step a), respectively the target nucleic acid containing eluate of step d) is heated at least to a temperature of 35° C., at least 40° C., or at least 50° C. and preferably is heated to a temperature of at least 55° C. during incubation. Using respective higher temperatures during incubation is in particularly favourable, if proteolytic enzymes are used as protein-degrading compounds that show their optimal, respective highest activity at higher temperatures.

Furthermore, it is preferred that the incubation during step a) and/or step d) is performed while agitating the sample of step a), respectively the target nucleic acid containing eluate of step d). Non-limiting examples of agitation include shaking, stirring, mixing, or vibrating. In certain aspects, agitation comprises shaking. The shaking can be one, two, or three dimensional shaking. A variety of shaking or agitating devices can be used. Non-limiting examples include the Thermomixer (Eppendorf), TurboMix (Scientific Industries), Mo Bio Vortex Adapter (Mo Bio Laboratories), Microtube holder vortex adapter (Troemner), and the Microtube foam rack vortex attachment (Scientific Industries). Agitating can be performed for example in a mixer with at least 50 rpm, at least 100 rpm, at least 200 rpm or at least 500 rpm. Preferably, heating and agitation is simultaneously performed, for example by using a thermomixer or an equivalent apparatus that allows simultaneous heating and agitation. These conditions are particularly favourable when using a proteolytic enzyme as protein-degrading compound.

When using at least one proteolytic enzyme as protein-degrading compound, incubation conditions are used that ensure that said enzyme works efficiently and is catalytically active. The conditions depend on the proteolytic enzyme used and are known, respectively determinable by the skilled person. Preferably, the incubation in step a) and/or d) is performed in the presence of salts and/or ions that promote and/or maintain the activity of the proteolytic enzyme. Suitable salts include but are not limited to NaCl, KCl, $MgCl_2$, or $CaCl_2$ or chaotropic agents such as chaotropic salts.

The incubation in step a) and/or step d) is preferably performed in the presence of chaotropic agents. This is particularly preferred in case RNA is isolated as target nucleic acid. Any chaotropic agent can be used for that purpose that causes disorder in a protein or nucleic acid by, for example, but not limited to altering the secondary, tertiary or quaternary structure of a protein or a nucleic acid while leaving the primary structure intact. Preferred chaotropic agents that can be used during incubation with the at least one protein-degrading compound in step a) and/or step d) include but are not limited to guanidinium hydrochloride, guanidinium thiocyanate, guanidinium isothiocyanate, sodium thiocyanate, sodium iodide, sodium perchlorate, sodium trichloroacetate, sodium trifluoroacetate, urea and the like.

The incubation with the at least one protein-degrading compound in step a) and/or step d) is usually performed at a pH value that does not lead to a degradation of the target nucleic acid. Furthermore, when using a proteolytic enzyme as protein-degrading compound, a pH value should be used wherein the proteolytic enzyme is active. Preferably, the incubation with the at least one protein-degrading compound in step a) and/or step d) is performed at a pH between 4.3 to 9, 6 to 8 and, preferably, is performed at a neutral pH value.

In order to ensure efficient degradation of the proteins, the sample in step a) respectively the target nucleic acid containing eluate in step d) should be incubated for a period of at least 3 minutes, preferably at least 5 minutes in order to ensure efficient protein degradation. According to a preferred embodiment, the incubation is performed in step a) for at least 5 minutes and in step d) for at least 10 minutes.

According to a preferred embodiment, the incubation in step a) and step d) is performed under heating, agitation, in the presence of chaotropic agents, a pH of 6 to 8, preferably a neutral pH, and for an incubation period of at least 3, preferably at least 5 minutes.

According to a preferred embodiment, the protein-degrading compound is a proteolytic enzyme. A proteolytic enzyme refers to an enzyme that catalyzes the cleavage of peptide bounds, for example in proteins, polypeptides, oligopeptides and peptides. Exemplary proteolytic enzymes include but are not limited to proteinases and proteases in particular subtilisins, subtilases, alkaline serine proteases and the like. Subtilases are a family of serine proteases, i.e. enzymes with a serine residue in the active side. Subtilisins are bacterial serine protease that has broad substrate specificities. Subtilisins are relatively resistant to denaturation by chaotropic agents, such as urea and guanidine hydrochloride and anionic detergents such as sodium dodecyl sulfate (SDS). Exemplary subtilisins include but are not limited to proteinase K, proteinase R, proteinase T, subtilisin, subtilisin A, QIAGEN Protease and the like. Discussions of subtilases, subtilisins, proteinase K and other proteases may be found, among other places in Genov et al., Int. J. Peptide Protein Res. 45: 391-400, 1995. Preferably, the proteolytic enzyme is proteinase K. Using a proteolytic enzyme such as proteinase K has the advantage that the proteolytic enzyme also digests itself during the incubation. The incubation using the proteolytic enzyme is performed under conditions wherein the proteolytic enzyme is active.

In non-limiting aspects, the proteolytic enzyme is used in a concentration in incubation step a) and/or d) between about 0.001 mg/ml to about 50 mg/ml. In other embodiments the range can be between from about 0.01 mg/ml to about 5 mg/ml, or between about 0.2 mg/ml to about 1.0 mg/ml.

According to one embodiment, one or more additional additives are present during incubation step a) and/or d). E.g. additives can be added which support the lysis of the sample, the degradation of the proteins and/or which preserve the target nucleic acid in the incubation mixture. Non-limiting examples include but are not limited to chelating agents, detergents, buffering agents, alkaline agents, nuclease inhibitors and beta-mercaptoethanol.

According to one embodiment, the incubation in step a) and/or step d) is performed in the presence of at least one nuclease inhibitor. Preferably, an RNase inhibitor is used when isolating RNA and a DNase inhibitor when isolating DNA. It is also within the scope of the present invention to use a combination of such nuclease inhibitors. Suitable nuclease inhibitors are known in the prior art and thus, need no detailed description.

According to one embodiment, the binding in step b) and/or step e) is performed in the presence of chaotropic agents and/or in the presence of alcohol.

The concentration of chaotropic agents used during binding in step b) and/or step e) may lie in a range of 0.05M up to the saturation limit. Preferred concentration ranges lie, depending on the chaotropic agent used, within 0.1M to 7M, 1M to 7M, 1.5M to 6M and 2M to 4M. Suitable chaotropic agents include but are not limited to guanidinium hydrochloride, guanidinium thiocyanate, guanidinium isothiocyanate, sodium thiocyanate, sodium iodide, sodium perchlorate, urea and the like and in particular preferred are sodium perchlorate, sodium trichloroacetate and sodium trifluoroacetate.

Thus, according to one embodiment which is particularly preferred when isolating RNA as target nucleic acid, a chaotropic salt is used as chaotropic agent that comprises a chaotropic anion selected from the group consisting of trichloroacetate, perchlorate and trifluoroacetate. Said chaotropic anion selected from the group consisting of trichloroacetate, perchlorate and trifluoroacetate may be present during binding in a concentration of at least 0.05M up to the saturation limit. According to one embodiment, the concentration lies in a range from 0.05M to 4M. According to one embodiment, the concentration lies in a range from 0.05M to 3M and preferably, in a range from 0.05M to 2M. According to a very preferred embodiment, the concentration of said chaotropic anion selected from the group consisting of trichloroacetate, perchlorate and trifluoroacetate lies in a range from 0.1M to 1M. Most preferred, the concentration of said chaotropic anion is less than 1M and lies in a range from 0.1M to 0.9M or 0.1M to 0.8M. Accordingly, the chaotropic salt comprising a chaotropic anion selected from the group consisting of trichloroacetate, perchlorate and trifluoroacetate is preferably present during binding in the concentrations described above for the chaotropic anion according to the present invention in particular when the salt comprises a monovalent cation. As cation, an alkali metal ion such as preferably sodium can be used. Therefore, according to one embodiment the chaotropic agent is selected from the group consisting of sodium perchlorate, sodium trichloroacetate and sodium trifluoroacetate. These chaotropic salts are particularly well suitable for the isolation of RNA, including small RNA species. Preferably, sodium trichloroacetate is present in the binding composition in a concentration of 0.1M to less than 1M, preferably in a concentration of 0.1M to 0.7M. If desired, also other chaotropic salts such as e.g. the commonly used guanidinium salts can be used in addition to the chaotropic salt comprising a chaotropic anion selected from the group consisting of trichloroacetate, perchlorate and trifluoroacetate.

As alcohol, it is preferred to use short chained branched or unbranched alcohols with preferably one to 5 carbon atoms. Examples are methanol, ethanol, propanol, isopropanol and butanol. Also mixtures of alcohol can be used. The alcohol is preferably selected from isopropanol and ethanol, particularly well suitable is isopropanol when isolating RNA as target nucleic acid. Preferably, the method according to the present invention does not involve the use of phenol and/or chloroform.

The alcohol may be comprised in the binding mixture of step b) and/or step e) in a concentration of 10% v/v to 90% v/v, in particular 15% v/v to 80% v/v, 20% to 80% v/v. For isolating RNA as target nucleic acid which also comprises small RNA, it is beneficial to use an alcohol concentration of 30% v/v, preferably 40% v/v to 80% v/v during binding and thus in the binding mixture. Higher concentrations of alcohol improve the binding and thus isolation of short nucleic acids (usually having a size of 500 nt or less), in particular small RNA species. Most preferred is an alcohol concentration of $\geq 40\%$ v/v to $\leq 80\%$ v/v or of $\geq 40\%$ v/v to $\leq 65\%$ v/v during binding when intending to isolate RNA which includes small RNA.

Optionally, one or more detergents can be used for binding the target nucleic acid to the solid phase in step b) and/or step e). Preferably, ionic and/or non-ionic detergents are used as detergent. Preferably, a non-ionic detergent is used in a concentration of at least 5%. Said detergent can be added, e.g., with a binding buffer.

Furthermore, a biological buffer can be used for binding. Non-limited examples of biological buffers include but are not limited to HEPES, MES, MOPS, TRIS, BIS-TRIS Propane and others. Preferably, a Tris buffer is used for binding the target nucleic acid to the solid phase.

Therefore, according to one embodiment of the method of the present invention, for binding the target nucleic acid to the solid phase and accordingly, for obtaining suitable binding conditions in the binding mixture of step b) and/or step e), the sample of step a) (respectively the eluted target nucleic acid processed in incubation step d)) is contacted in step b) (respectively in step e)) with a binding buffer which comprises at least one alcohol and at least one chaotropic agent and optionally a biological buffer, preferably Tris to bind the target nucleic acid to the solid phase. Optionally, the binding buffer may also comprise a detergent as is described above. However, the components can also be added separately to form a suitable binding composition. Preferably, the binding buffer pH is in a range that includes 8. According to one embodiment, the binding buffer pH is in the range from pH 7.0 to 9, preferably 7.5 to 8.5; most preferred the binding buffer has a pH of 8.

According to one embodiment, one or more washing steps are performed between steps b) and c) and/or after step e) while the target nucleic acid is bound to the solid phase. For this purpose common washing solutions may be used. According to one embodiment, the solution used for washing comprises at least one chaotropic agent, at least one alcohol, at least one detergent and/or at least one buffering component. Chaotropic agents that can be used in the washing solutions include but are not limited to guanidinium hydrochloride, guanidinium thiocyanate, guanidinium isothiocyanate and sodium iodide. Furthermore, chaotropic salts can be used which comprise a chaotropic anion selected form the group consisting of trichloroacetate, perchlorate and trifluoroacetate. Examples of respective chaotropic salts are alkali salts like sodium perchlorate, sodium trichloroacetate and sodium trifluoroacetate. As alcohol, short chained branched or unbranched alcohols with preferably one to 5 carbon atoms can be used for washing, respectively in the washing solution. Examples are methanol, ethanol, propanol, isopropanol and butanol. Preferably, isopropanol and/or ethanol are used. Preferably, the washing solution comprises at least 50% alcohol and at least 1M chaotropic salt, preferably at least 2M chaotropic salt. Furthermore, the washing solution may comprise a detergent. Preferably, ionic and/or non-ionic detergents are used as detergent. Preferably, a non-ionic detergent is used in a concentration of at least 5%. It is also within the scope of the present invention to perform additional intermediate steps than the ones described herein. However, according to certain embodiments, no additional steps other than the ones described herein are performed.

A further suitable washing solution which can be used alternatively or also in addition to the washing solutions described above comprises an alcohol and a biological buffer. Suitable alcohols and biological buffers are described above. Preferably, isopropanol or ethanol, most preferred ethanol is used for this second washing step. Preferably, ethanol is used in a concentration of at least 70% v/v, preferably at least 80% v/v. The biological buffer is preferably Tris at a pH of approx. 7 to 8.

The degree of purity of the isolated nucleic acid can be determined by suitable methods known in the prior art. According to one embodiment, the degree of purity is determined by spectrophotometric analysis. One common way to determine the degree of protein contaminations is the determination of the 260:280 ratio. Nucleic acids adsorb light at 260 nm, proteins at 280 nm. For pure DNA, the $A_{260/280}$ is approx. 1.8 and for pure RNA the $A_{260/280}$ is approx. 2. Because nucleic acids have a higher extinction coefficient at 260 nm and 280 nm compared to that of proteins, even little differences in the 260/280 ratios are important because they show varying protein contents. The lower the 260/280 ratio, the higher is the amount of protein contamination in the analysed nucleic acid sample. With respect to RNA, it is usually acceptable with respect to the purity, if the 260/280 ratio of the isolated RNA lies within the range of 1.8 to 2.2, preferably 1.9 to 2.1. However, it is not only important that a nucleic acid isolation procedure is able to reach this purity under certain conditions or once in while when processing a specific sample. Conversely, it is important that these purities are reached reliably and continuously even if different samples and also if samples comprising varying amounts of proteins (such as blood or blood products) are processed. The method according to the present invention achieves this because it provides the isolated target nucleic acids continuously with a reliable purity that lies within a given range even if strong binding conditions are used, or if samples are processed that comprise a high and also a varying amounts of protein. Therefore, the method according to the present invention allows the isolation of target nucleic acid with high yield and a reliable purity if different samples and also samples comprising varying amounts of proteins (such as blood or blood products) are processed. According to one embodiment for isolating RNA as target nucleic acid, the 260/280 ratio of 80%, preferably 90%, most preferred 95% of the purified RNA lies within the range of 1.8 to 2.2, preferably 1.85 to 2.1. Thus, when performing the method 100 times, in 95 cases the respective purity is reached.

The term "sample" is used herein in a broad sense and is intended to include a variety of sources that contain nucleic acids. The sample may be a biological sample but the term also includes other, e.g. artificial samples which comprise nucleic acids. Exemplary samples include, but are not limited to, whole blood; red blood cells; white blood cells; buffy coat; swabs, including but not limited to buccal swabs, throat swabs, vaginal swabs, urethral swabs, cervical swabs, throat swabs, rectal swabs, lesion swabs, abcess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; and tissues, including but not limited to, liver, spleen, kidney, lung, intestine, brain, heart, muscle, pancreas, cell cultures, as well as lysates, extracts, or materials obtained from any cells and microorganisms and viruses that may be present on or in a sample and the like. Materials obtained from clinical or forensic settings that contain nucleic acids are also within the intended meaning of the term sample. Furthermore, the skilled artisan will appreciate that lysates, extracts, or materials or portions thereof obtained from any of the above exemplary samples are also within the scope of the term sample. Preferably, the sample is a biological sample derived from a human, animal, plant, bacteria or fungi. In particular, the term "sample" refers to a nucleic acid containing sample which also comprises proteins. Preferably, the sample is selected from the group consisting of cells, tissue, bacteria, virus and body fluids such as for example blood, blood products such as buffy coat, plasma and serum, urine, liquor, sputum, stool, CSF and sperm, epithelial swabs, biopsies, bone marrow samples and tissue samples, preferably organ tissue samples such as lung and liver. Preferably, the sample is selected from whole blood and blood products such as buffy coat, serum or plasma.

The term "nucleic acid" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. Nucleic acids include, but are not limited to, gDNA; circular DNA; circulating DNA; hnRNA; mRNA; noncoding RNA (ncRNA), including but not limited to rRNA, tRNA, miRNA (micro RNA), siRNA (small interfering RNA), snoRNA (small nucleolar RNA), snRNA (small nuclear RNA) and stRNA (small temporal RNA); fragmented nucleic acid; nucleic acid obtained from subcellular organelles such as mitochondria or chloroplasts; and nucleic acid obtained from microorganisms, parasites, or DNA or RNA viruses that may be present in a biological sample. Synthetic nucleic acid sequences that may or may not include nucleotide analogs that are added or "spiked" into a biological sample are also within the scope of the invention. Small RNA or the term small RNA species in particular refers to RNA having a length of less than 500 nt, 400 nt, 300 nt or 100 nt and includes but is not limited to miRNA, siRNA, other short interfering nucleic acids, snoRNAs and the like.

The method according to the present invention pertains to a method for purifying at least a target nucleic acid. As becomes apparent from the described examples of samples that can be processed according to the method of the present invention, a sample may comprise more than one type of nucleic acid. Depending on the intended use, it may be desirous to isolate all types of nucleic acids from a sample ((e.g. DNA and RNA which would then both be target nucleic acids) or only certain types or a certain type of nucleic acid (e.g. only RNA but not DNA or vice versa). All these variants are within the scope of the present invention.

Thus, according to one embodiment, the sample comprises at least one non-target nucleic acid and at least one target nucleic acid.

According to one embodiment, the method according to the present inventions comprises an intermediate step after step a) that is performed prior to step b) that removes at least a portion of non-target nucleic acid. Preferably, the non-target nucleic acid is removed by binding at least a portion of the non-target nucleic acid under appropriate conditions to a solid phase and then separating the non-target nucleic acid bound to the solid phase from the remaining sample comprising the target nucleic acid. This can be achieved e.g. by the addition of a suitable solid phase under conditions wherein mainly the non-target nucleic acids are bound to the solid phase. Suitable methods for selectively removing a non-target nucleic acid from a target nucleic acid are for example described in EP 0 880 537 and WO 95/21849, herein incorporated by reference.

When intending to isolate (only) RNA as target nucleic acid, the non-target nucleic acid is usually DNA.

In order to further reduce the amount of non-target nucleic acids, an intermediate step for degrading non-target nucleic acids using a suitable enzyme can be performed prior to step d) and preferably after step c). According to one embodiment wherein RNA is isolated as target nucleic acid, a DNase treatment is accordingly performed prior to step d). Said DNase digest can be performed at any step, however, it is preferred that the DNase treatment is performed after step c) and prior to step d). As the conditions for performing a DNase digest are well known in the prior art, they do not need further description here. Performing the DNase digest prior to step d) has the advantage that the DNase is also degraded during the second protein degradation step d) and accordingly, the DNase does not contribute, respectively contributes less to the amount of protein contaminations contained in the isolated target nucleic acids. Basically the same applies when isolating DNA as target nucleic acid and accordingly when using an RNase for degrading RNA as non-target nucleic acid.

As solid phase, any material that is capable of binding nucleic acids that are present in or are released from a sample can be used and include a variety of materials that are capable of binding nucleic acids under suitable conditions. Exemplary solid phases that can be used in conjunction with the present invention include, but are not limited to, compounds comprising silica, including but not limited to, silica particles, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina;

polymeric supports, diethylaminoethyl- and triethylaminoethyl-derivatized supports, hydrophobic chromatography resins (such as phenyl- or octyl Sepharose) and the like. The term solid phase is not intended to imply any limitation regarding its form or design. Thus, the term solid phase encompasses appropriate materials that are porous or nonporous; permeable or impermeable; including but not limited to membranes, filters, sheets, particles, magnetic particles, beads, gels, powders, fibers, and the like. According to one embodiment, the surface of the solid phase such as e.g. the silica solid phase is not modified and is, e.g., not modified with functional groups.

According to a preferred embodiment, a solid phase comprising silica is used. It was found that the problem of protein contaminations in particular occurs when using silica particles as solid phase. Thus, the present invention in particular solves the problem of protein contaminations when using silica particles as solid phase. In particular preferred is the use of silica particles that can be used in form of beads and which preferably have a particle size of about 0.02 to 30 µm, more preferred 0.05 to 15 µm and most preferred of 0.1 to 10 µm. To ease the processing of the nucleic acid binding carrier, preferably magnetic silica particles are used. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Other magnetic silica particles are also known from the prior art and are e.g. described in WO 98/31840, WO 98/31461, EP 1 260 595, WO 96/41811 and EP 0 343 934 and also include for example magnetic silica glass particles.

According to one embodiment, which is particularly preferred when RNA is isolated from a biological sample such as whole blood or blood products, the nucleic acids contained in the sample are stabilised preferably immediately after the biological sample has been taken from its natural environment in order to preserve the status quo of the sample and in particular the transcription pattern. This is particularly beneficial in the medical and diagnostic field.

Thus, according to one embodiment, the sample is mixed with a nucleic acid storage stabilization composition for stabilizing nucleic acids in said sample prior to isolating the nucleic acids from said sample. According to one embodiment, said stabilization composition comprises
a) a cationic compound of the general formula:

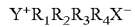
$Y^+R_1R_2R_3R_4X^-$ wherein Y represents nitrogen or phosphor, preferably nitrogen $R_1R_2R_3$ and $R_4$ independently, represent a branched or unbranched $C_1$-$C_{20}$-alkyl group, a $C_6$-$C_{20}$-aryl group and/or a $C_6$-$C_{26}$ aralkyl group;

$X^-$ represents an anion of an inorganic or organic, mono- or polybasic acid; and b) at least one proton donor, wherein the proton donor is preferably present in the composition in a concentration of above 50 mM to saturation and wherein the proton donor is preferably selected from the group consisting of saturated aliphatic monocarboxylic acids, unsaturated alkenyl-carboxylic acids, saturated and/or unsaturated aliphatic $C_2$-$C_6$-dicarboxylic acids, aliphatic hydroxyl-di- and tricarboxylic acids, aliphatic ketocarboxylic acids, amino acids or the inorganic acids or the salts thereof, on their own or in combination.

Preferably, $R_1$ denotes a higher alkyl group with 12, 14 or 16 carbon atoms and $R_2$, $R_3$ and $R_4$ each represent a methyl group.

Preferably, the anion $X^-$ represents an anion of hydrohalic acids or anions of mono- or dibasic organic acids, most preferred the anion $X^-$ is selected from the group consisting of bromide, chloride, phosphate, sulphate, formate, acetate, propionate, oxalate, malonate, succinate or citrate.

Preferably, the proton donor is selected from the group consisting of saturated aliphatic monocarboxylic acids, unsaturated alkenyl-carboxylic acids, saturated and/or unsaturated aliphatic $C_2$-$C_6$-dicarboxylic acids, aliphatic ketocarboxylic acids, amino acids or the inorganic acids or the salts thereof, and combinations thereof. Preferably, the aliphatic monocarboxylic acid comprises a $C_1$-$C_6$-alkyl-carboxylic acid selected from the group consisting of acetic acid, propionic acid, n-butyric acid, n-valeric acid, isovaleric acid, ethyl-methyl-acetic acid (2-methyl-butyric acid), 2,2-dimethylpropionic acid (pivalic acid), n-hexanoic acid, n-octanoic acid, n-decanoic acid or n-dodecanoic acid (lauric acid) or mixtures thereof. Preferably, the aliphatic alkenyl-carboxylic acid is selected from the group consisting of acrylic acid (propenoic acid), methacrylic acid, crotonic acid, isocrotonic acid or vinylacetic acid or mixtures thereof. Preferably, the saturated aliphatic $C_2$-$C_6$-dicarboxylic acid is selected from the group consisting of oxalic acid, malonic acid, succinic acid, glutaric acid or adipic acid or mixtures thereof. Most preferred, the aliphatic dicarboxylic acid is oxalic acid or succinic acid or mixtures thereof. Preferably, the aliphatic hydroxy-di- and -tricarboxylic acids are selected from the group consisting of tartronic acid, D-(+), L-(−) or DL-malic acid, (2R,3R)-(+)-tartaric acid, (2S,3S)-(−)-tartaric acid, meso-tartaric acid and citric acid or mixtures thereof. Most preferred, the unsaturated dicarboxylic acid is maleic and/or fumaric acid or mixtures thereof. Preferably, the unsaturated tricarboxylic acid is aconitic acid. Preferably, the aliphatic ketodicarboxylic acids are mesoxalic acid or oxaloacetic acid, or mixtures thereof. Preferably, the amino acids are selected from the group consisting of aminoacetic acid (glycine), alpha-aminopropionic acid (alanine), alpha-amino-iso-valeric acid (valine), alpha-amino-iso-caproic acid (leucine) and alpha-amino-beta-methylvaleric acid (isoleucine), or mixtures thereof.

Preferably, the stabilising composition is present in an aqueous solution. Preferably, the cationic compound is comprised in a concentration in the range from 0.01 weight percent to 15 weight percent.

Suitable stabilising solutions are also described in detail e.g. in U.S. Pat. No. 7,270,953, herein incorporated by reference.

Complex samples that are stabilised as is described above are a particular challenge for isolating nucleic acids due to the additives in the stabilising solution and the high protein content of the samples. The method of the present invention overcomes these difficulties and allows the isolation of RNA including small RNA if desired with good yield and high purity from respectively stabilised samples and in particular complex biological samples such as whole blood and blood products such as buffy coat, serum and/or plasma or tissue samples, in particular organ tissue samples e.g. obtained from lung or liver. Therefore, the method of the present invention is particularly useful in the medical and in particular in the diagnostic field.

According to a preferred embodiment of the present invention, a method for purifying RNA from a sample comprising at least RNA and DNA is provided, said method comprising at least the following steps a) incubating the sample with at least one proteolytic enzyme in the presence of a chaotropic agent and by heating the sample to at least 40° C.,
  removing at least a portion of the DNA by binding DNA to a first solid phase and separating the DNA bound to said first solid phase from the remaining sample comprising the RNA,
b) binding the RNA to a second solid phase, wherein at least one chaotropic agent and alcohol in a concentration 30% v/v is used during this binding step b),
  performing at least one washing step for washing the RNA bound to said second solid phase,
c) eluting the RNA from said second solid phase,
d) incubating the eluted RNA with at least one proteolytic enzyme in the presence of a chaotropic agent and by heating the sample to at least 40° C.,
e) binding the RNA again to a solid phase wherein at least one chaotropic agent and alcohol in a concentration 30% v/v is used during this binding step e),
  performing at least one washing step for washing the RNA bound to the solid phase,
f) optionally eluting the bound target nucleic acid from the solid phase.

As is described above, the method of the present invention is in particular suitable for isolating RNA with high purity and thus low protein contaminations from complex samples, which comprise large amounts of protein even if binding conditions are used that promote binding and thus the co-purification of protein contaminations. Suitable conditions for performing the individual steps are described in detail above, it is referred to the above disclosure which also applies to this specific embodiment for isolating RNA. This specific embodiment of the method according to the present invention is in particular suitable for isolating RNA including small RNAs such as miRNA from a sample which comprises high amounts of proteins such as blood and blood products. Suitable binding conditions for isolating RNA including small RNA are described in detail above. It is referred to the above disclosure which also applies here.

EXAMPLES

1. RNA Isolation Protocols

Total RNA was isolated from whole blood (2.5 ml) from 12 different donors in triplicates in PAXgene Blood RNA tubes which comprise a stabilisation solution. Suitable stabilisation solutions are also described above. The PAXgene Blood RNA tubes (PreAnalytiX) comprising the stabilised sample were further processed according to the instruction manuals for the commercially available kits QIAsymphony PAXgene Blood RNA Kit (PreAnalytiX), a modified version thereof for also isolating small RNA species such as miRNA or the method according to the present invention.

The stabilised sample was processed as follows:
a) QIAsymphony PAXgene Blood RNA (PreAnalytiX)

The detailed protocol is described in the corresponding handbook. Thus, the respective protocol is only briefly described herein:
1. The PAXgene Blood RNA tubes were centrifuged for 10 minutes at 3000-5000× g using a swing-out rotor.
2. After centrifugation, the supernatant was removed by decanting. The supernatant was discarded and the pellet was saved for resuspension in step 3.
3. 300 µl Buffer BR1 was added per tube. The tubes were closed and the pellet was thoroughly resuspended by vortexing. A multitube vortexer was used for resuspension at full speed for 30 seconds, respectively until the pellets were completely resuspended.
4. The closures were removed and discarded.
5. The robotic system QIAsymphony SP was used for further processing. The required reagent cartridge for the PAXgene Blood RNA isolation and consumables were loaded into the "Reagents and Consumable" drawer. Furthermore, the required elution rack was loaded into the "Eluate" drawer.
6. The samples from step 4 were placed into the appropriate sample carrier and loaded into the "Sample" drawer. Afterwards, the samples were processed by the QIAsymphony with the corresponding program. In brief, the robotic system QIAsymphony processed the probes by adding the lysis buffer BR2, proteinase K and the MagAttract beads. First, DNA was bound to the beads and removed. Afterwards, further magnetic beads were added in addition to the binding buffer QSB1. Afterwards, the complexes were pre-washed with buffer QSB1 and buffer BR4.
7. The samples were pre-eluted with buffer BR5 and remaining DNA was digested. The RNA was rebound by adding the buffer QSB2. Afterwards, further washing steps were performed, the complexes were dried and the RNA eluted.

b) Modified QIAsymphony Protocol for Including Small RNAs Such as miRNAs

The modified QIAsymphony PAXgene Blood protocol for also isolating small RNAs such as miRNAs was performed on the QIAsymphony robotic system. In brief, the following steps were performed:
1. The PAXgene Blood RNA tube was centrifuged for 10 min at 3.000 to 6.000 rpm. The pellet was resuspended by the addition of a buffer (300 µl) comprising ammonium acetate and vortexing. A suitable buffer is the buffer BR1 (QIAGEN).
2. Further lysis agents were added, preferably Proteinase K (40 µl) and a lysis buffer (230 µl) comprising more than 3M of a chaotropic salt, preferably GITC. A suitable buffer is the buffer BR2 (QIAGEN). Afterwards, the sample was incubated for 10 min at 56° C., 100 rpm.
3. MagAttract beads (QIAGEN) were added to bind and remove DNA together with the silica particles.
4. For binding of the RNA, additional MagAttract beads were added (60 µl) and 1500 µl of a binding buffer according to the present invention comprising 80% isopropanol (or ethanol), 0.6M sodium perchlorate, sodium trifluoroacetate or sodium trichloroacetate respectively, and Tris.
5. Two washing steps were performed. The first washing step was performed with a buffer comprising isopropanol, GTC and a detergent; the second washing step was performed with a washing buffer comprising ethanol and Tris.
6. Afterwards, the RNA was pre-eluted with 250 µl of an elution buffer (e.g. BR5, QIAGEN) and a DNase digest was performed (225 µl buffer RDD (QIAGEN) and 25 µl DNase I stock solution (QIAGEN)).
7. For re-binding the RNA to the beads, 1400 µl of the same binding buffer (see above) was added. This second binding step ensures a good yield of small RNAs.
8. Afterwards, four additional washing steps were performed.
9. Total RNA was eluted by using a suitable elution buffer (BR5, QIAGEN). Also other common elution buffers such as water or a Tris-buffer can be used.

c) Method According to the Present Invention

The method according to the present invention was also performed on the QIAsymphony robotic system. The method corresponds to the method described in b) however, an additional proteinase K digest was performed after the DNase digest. In brief, the following steps were performed:

1. The PAXgene Blood RNA tube was centrifuged for 10 min at 3.000 to 6.000 rpm. The pellet was resuspended by the addition of a buffer (300 µl) comprising ammonium acetate and vortexing. A suitable buffer is the buffer BR1 (QIAGEN).

2. Further lysis agents were added, preferably Proteinase K (20 µl) and a lysis buffer (230 µl) comprising more than 3M of a chaotropic salt, preferably GITC. A suitable buffer is the buffer BR2 (QIAGEN). Afterwards, the sample was incubated for 10 min at 56° C., 100 rpm.

3. MagAttract beads (QIAGEN) were added to bind and remove DNA together with the silica particles.

4. For binding of the RNA, additional MagAttract beads were added and 1500 µl of a binding buffer according to the present invention comprising 80% isopropanol (or ethanol), 0.6M sodium perchlorate, sodium trifluoroacetate or sodium trichloroacetate respectively, and Tris.

5. Two washing steps were performed. The first washing step was performed with a buffer comprising isopropanol, GTC and a detergent; the second washing step was performed with a washing buffer comprising ethanol and Tris.

6. Afterwards, the RNA was pre-eluted with 250 µl of an elution buffer (e.g. BR5, QIAGEN) and a DNase digest was performed (225 µl buffer RDD (QIAGEN) and 25 µl DNase I stock solution (QIAGEN)).

7. Then, a second proteinase K digestion step was performed. For this purpose, 20 µl proteinase K and a lysis buffer (200 µl) comprising more than 3M of a chaotropic salt, preferably GITC was added (a suitable buffer is BR2, QIAGEN) and the sample was incubated for 5 min at 56° C., 100 rpm.

8. For re-binding the RNA to the beads, 1400 µl of the same binding buffer according to the present invention (see above) was added. This second binding step ensures a good yield of small RNAs.

9. Afterwards, four additional washing steps were performed. For this purpose, the washing buffers QSB1, AW1 and BR4 (all QIAGEN) can be used.

9. Total RNA was eluted by using a suitable elution buffer (BR5, QIAGEN). Also other common elution buffers such as water or a Tris-buffer can be used.

2. Results

The results are shown in FIGS. 1.1 to 5.4.

FIG. 1.1 shows that the QIAsymphony PAXgene Blood RNA protocol renders the RNA with high and reliable purity which lies stably and consistently in the range of 1.8 to 2.0. The modified QIAsymphony PAXgene Blood RNA protocol which is designed to increase the overall yield of RNA and in particular the yield of small RNA such as miRNA in the isolated total RNA does not provide optimal purities, because the 260/280 ratio often lied below 1.8 and furthermore, showed high variations. As can be seen in FIG. 1.2, also the mean purity is below 1,8.

This decrease in purity is attributable to the fact that this modified QIAsymphony PAXgene Blood RNA (miRNA) protocol uses a strong binding chemistry (strong chaotropic agents and a high alcohol concentration). These binding conditions have the advantageous effect that the total RNA yield is increased and that also small RNA species are bound and thus isolated with high efficiency. However, these strong binding conditions have the draw-back that protein contaminations also bind to the silica particles, thereby decreasing the purity below an acceptable level and furthermore, resulted in variations in the obtained purity what is not acceptable in particular in automated processes.

FIG. 2.1 and FIG. 2.2 show the effect of the second proteinase K digest on the RNA purity. These figures show that the method according to the present invention provided purities that are comparable to the QIAsymphony PAXgene Blood RNA protocol, even though a binding chemistry was used which not only increases the binding of the small RNAs, but also increases the binding of protein contaminations (see also FIGS. 1.1 and 1.2). The purity of most samples lied within the range of 1.8 to 2.2, similar to the QIAsymphony PAXgene Blood RNA protocol. FIG. 2.2 shows the main purity obtained by the different methods. The results show that the protocol according to the present invention showed considerable improvements over conventional methods because excellent purity was continuously achieved while providing the RNA with high yield and while also isolating the small RNA species.

FIG. 3 shows the effect of the additional proteinase K digest on the overall yield. As can be seen, the protocol according to the present invention (in the protocol invention I, rebinding was performed for 2.5 min, in invention II, rebinding was performed for 5 min) provided the RNA with a considerably increased yield compared to the QIAsymphony PAXgene Blood RNA protocol. Thus, the advantage of the strong binding chemistry with respect to the increase in yield was maintained while the drawback of the strong binding chemistry with respect to the protein contaminations was avoided.

Figure 4:
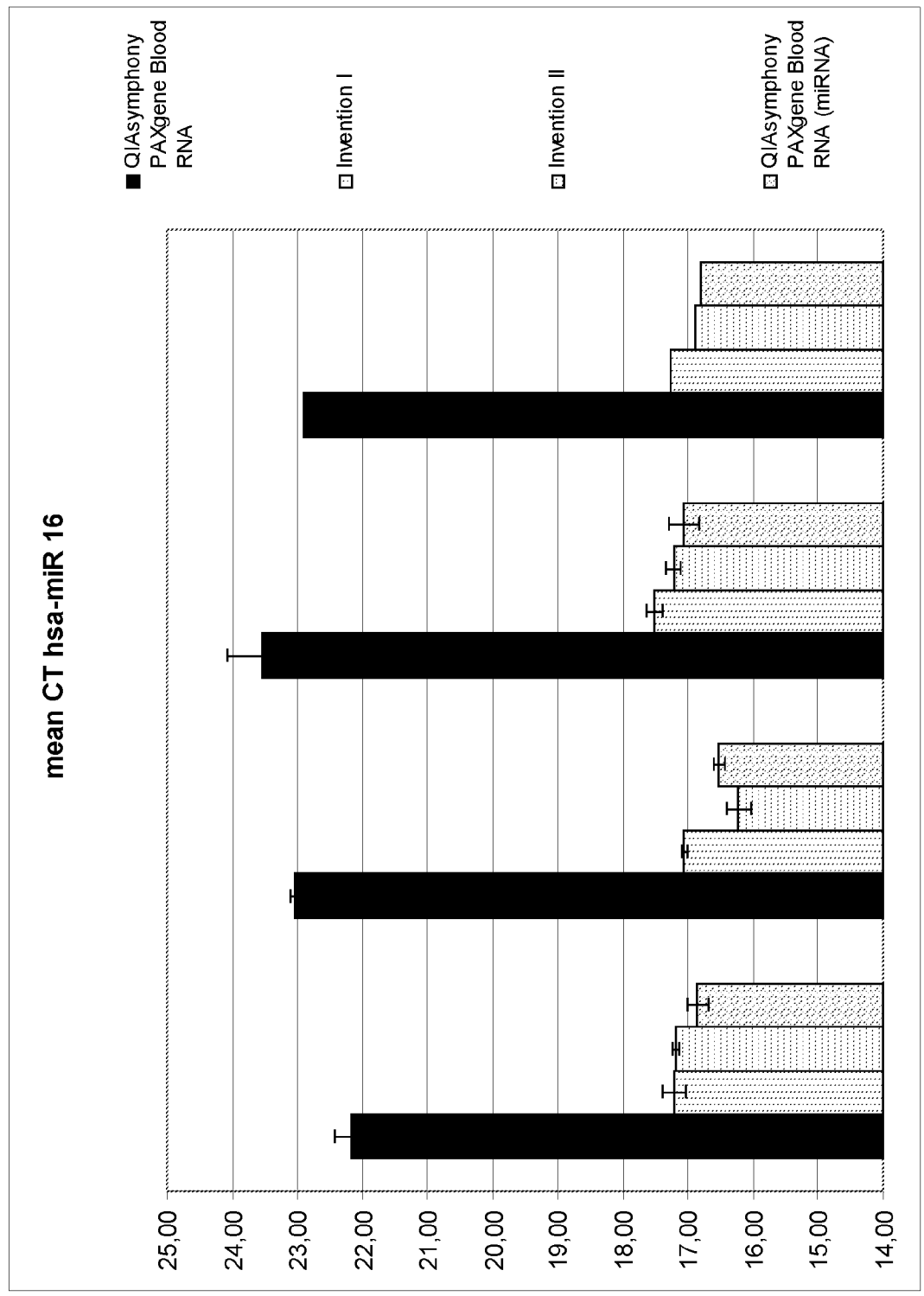

FIG. 4 shows the $C_T$ values of a RT-PCR that was performed to analyse the miRNA yield in the obtained RNA by determining the expression of has-miR 16. The higher the $C_T$ value, the lower is the content of the respective miRNA in the isolated RNA. As can be seen, the method according to the present invention provided total RNA which comprised the small RNA species with good yield, while the QIAsymphony PAXgene Blood RNA protocol which uses a less strong binding chemistry did not provide the small RNA species with high yield as can be derived from the high $C_T$ value. This demonstrates that the method according to the invention allows to also isolate small nucleic acids due to the strong binding chemistry, while providing good purity.

FIGS. 5.1 to 5.4 show a comparison of the purity of the QIAsymphony PAXgene Blood RNA kit, the modified version for isolating miRNA (QIAsymphony PAXgene Blood miRNA) and the method according to the present invention. As can be seen, the method according to the present invention considerably improved the purity.

The invention claimed is:

1. A method for purifying at least one target nucleic acid from a sample, comprising:
   (A) incubating the sample with at least one protein-degrading compound,
   (B) binding the target nucleic acid to a first solid phase,
   (C) eluting the target nucleic acid from the first solid phase,
   (D) incubating the eluted target nucleic acid with at least one protein-degrading compound, and
   (E) binding the target nucleic acid again to a second solid phase,
   wherein the protein degrading compound of steps (A) and (D) is a proteolytic enzyme; and
   wherein binding in step (B), step (E), or both steps (B) and (E) are performed in the presence of an alcohol at a concentration of at least 30% v/v and at least one chaotropic agent.

2. The method of claim 1, wherein the incubation in step (A), step (D), or both steps (A) and (D) are performed under conditions comprising one or more of the following (a) heating,
(b) agitation,
(c) the presence of salts,
(d) the presence of chaotropic agents,
(e) a pH value of between 6 to 9, and
(f) an incubation period of at least 3 minutes.

3. The method of claim 1, wherein binding in step (B), step (E), or both steps (B) and (E) are performed under conditions having one or more of the following characteristics:
   (a) binding is performing in the presence of detergents,
   (b) binding is performed under conditions that also promote binding of proteins to the solid phase, and
   (c) binding is performed under conditions that promote binding of small nucleic acids.

4. The method of claim 3, wherein the target nucleic acid comprises RNA.

5. The method of claim 1, wherein one or more washing steps are performed between steps (B) and (C), after step (E), or both between steps (B) and (C) and after step (E).

6. The method of claim 5, wherein the solution used for washing comprises one or more selected from the group consisting of chaotropic agents, alcohols, detergents, and buffering components.

7. The method of claim 1, wherein the sample comprises at least one non-target nucleic acid and at least one target nucleic acid.

8. The method of claim 7, wherein the non-target nucleic acid is DNA, and the target nucleic acid is RNA.

9. The method of claim 7, further comprising removing non-target nucleic acids after step (A) and prior to step (B).

10. The method of claim 9, further comprising enzymatically degrading the remaining non-target nucleic acids prior to step (D).

11. The method of claim 1, wherein the sample is mixed with a nucleic acid stabilization composition, and wherein said stabilization composition comprises
    (1) a cationic compound of the general formula:
       $Y^+R_1R_2R_3R_4X^-$
       wherein Y represents nitrogen or phosphor,
       $R_1$, $R_2$, $R_3$, and $R_4$ independently, represent a branched or unbranched $C_1$-$C_{20}$–alkyl group, a $C_6$-$C_{20}$ aryl group and/or a $C_6$-$C_{26}$ aralkyl group;
       $X^-$ represents an anion of an inorganic or organic, mono-or polybasic acid; and
    (2) at least one proton donor.

12. The method of claim 11, wherein Y represents nitrogen.

13. A method for purifying RNA from a sample that comprises RNA and DNA, comprising:
    (A) (1) incubating the sample with at least one proteolytic enzyme in the presence of a chaotropic agent and by heating the sample to at least 40° C.,
        (2) removing at least a portion of the DNA by binding DNA to a first solid phase and separating the DNA bound to said first solid phase from the remaining sample comprising the RNA,
    (B) (1) binding the RNA to a second solid phase in the presence of at least one chaotropic agent and alcohol in a concentration ≥30% v/v,
        (2) performing at least one washing step for washing the RNA bound to said second solid phase,
    (C) eluting the RNA from said second solid phase,
    (D) incubating the eluted RNA with at least proteolytic enzyme in the presence of a chaotropic agent and by heating the sample to at least 40° C.,
    (E) (1) binding the RNA again to a third solid phase in the presence of at least one chaotropic agent and alcohol in a concentration ≥30% v/v, and
        (2) performing at least one washing step for washing the RNA bound to the solid phase.

14. The method of claim 1, wherein total RNA, including small RNAs, is isolated as target nucleic acid, and wherein said method results in 95% of the isolated nucleic acid having an $A_{260/280}$ between 1.8 and 2.2.

15. The method of claim 1, wherein the sample is a biological sample selected from body fluids, blood, blood products, tissue and bone marrow.

16. The method of claim 1, wherein the solid phase capable of binding nucleic acids is selected from the group consisting of solid phases comprising or consisting of silica, magnetic silica particles, diatomaceous earth, glass, alkyl-silica, aluminum silicate, borosilicate, nitrocellulose, hydroxyapatite, metal oxides, polymeric supports, membranes, and magnetic particles.

17. The method of claim 1, further comprising:
    (F) eluting the bound target nucleic acid from the second solid phase.

18. The method of claim 13, further comprising:
    (F) eluting the bound RNA from the third solid phase.

19. The method of claim 1, wherein the target nucleic acid comprises small RNAs.

20. The method of claim 1, wherein the first solid phase, the second solid phase, or both the first and second solid phases are beads.

21. The method of claim 1, wherein the sample comprises blood.

22. The method according to claim 1, wherein binding in step (B), step (E), or both steps (B) and (E) are performed in the presence of the alcohol at a concentration selected from the group consisting of 30% v/v to 90% v/v, 40% v/v to 90% v/v, 30% v/v to 80% v/v, 40% v/v to 80% v/v, 40% v/v to 70%, and 40% v/v to 65%.

23. The method according to claim 1, wherein binding in step (B), step (E), or both steps (B) and (E) are performed in the presence of the at least one chaotropic agent at a concentration selected from the group consisting of 0.05M up to the saturation limit, 0.1M to 4M, and 1M to 4M.

* * * * *